United States Patent [19]

Fryer et al.

[11] 4,014,883

[45] Mar. 29, 1977

[54] INDOLOQUINOLINES, INTERMEDIATES AND PROCESSES

[75] Inventors: Rodney Ian Fryer, North Caldwell; Robert Ye-Fong Ning, West Caldwell; Leo Henryk Sternbach, Upper Montclair; Armin Walser, West Caldwell, all of N.J.

[73] Assignee: Hoffmann-La Roche Inc., Nutley, N.J.

[22] Filed: July 16, 1975

[21] Appl. No.: 596,684

Related U.S. Application Data

[63] Continuation of Ser. No. 395,871, Sept. 10, 1973, abandoned, which is a continuation-in-part of Ser. No. 292,193, Sept. 25, 1972, abandoned.

[52] U.S. Cl. ............... 260/288 CF; 260/246 B; 260/247.2 A; 260/247.5 FP; 260/268 PC; 260/283 SY; 260/283 CN; 260/287 C; 260/289 K; 260/326.13 R; 260/326.14; 424/250; 424/258; 424/248.56; 424/248.57; 424/248.58

[51] Int. Cl.$^2$ ..................... C07D 471/04

[58] Field of Search ... 260/288 CF, 287 C, 268 PC, 260/247.2 A, 247.5 FP, 246 B, 247.5 FP, 283 CN

[56] References Cited

UNITED STATES PATENTS

| | | | |
|---|---|---|---|
| 3,326,920 | 6/1967 | Stanabach et al. | 260/288 CF |
| 3,420,834 | 11/1973 | Muller et al. | 260/288 CF |

OTHER PUBLICATIONS

Winterfeldt et al., Angew Chem. Internat. Edit., vol. 17 (1968) p. 466.
Peterson et al., Acta Chem. Scand., vol. 23 (1969) pp. 971-974.

*Primary Examiner*—Donald G. Daus
*Assistant Examiner*—Mary C. Vaughn
*Attorney, Agent, or Firm*—Samuel L. Welt; Bernard S. Leon; William G. Isgro

[57] ABSTRACT

Derivatives of 7H-indolo[2,3-c]quinolin-6(5H)-one and 7H-indolo[2,3-c]quinoline, prepared, inter alia, from the corresponding 3-azido-4-phenylcarbostyrils or corresponding N-(lower alkylamino)-3-(2-fluorophenyl)-indole-2-carboxamides, are described. The end products of the invention are useful as anti-tumor agents, i.e., they inhibit the growth of transplantable tumors.

15 Claims, No Drawings

INDOLOQUINOLINES, INTERMEDIATES AND PROCESSES

CROSS-REFERENCE TO RELATED APPLICATIONS

This is a continuation of application Ser. No. 395,871, filed Sept. 10, 1973, now abandoned, which in turn is a continuation-in-part of U.S. Pat. Application Ser. No. 292,193, filed Sept. 25, 1972, now abandoned.

BRIEF SUMMARY OF THE INVENTION

The invention relates to compounds of the formula

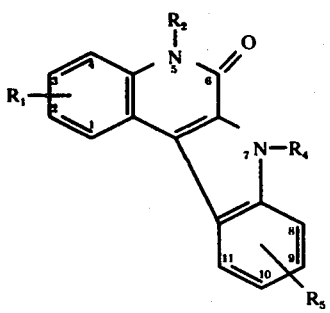

wherein $R_1$ and $R_5$, independently, are hydrogen, halogen, trifluoromethyl, lower alkyl, lower alkoxy, amino, cyano or nitro; $R_2$ and $R_4$, independently, are hydrogen, lower alkyl, cyano-lower alkyl, di-hydroxy-lower alkyl, 2,3-epoxy-propyl, loweralkenyl, or a radical of the formula

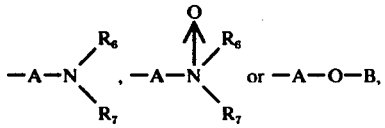

wherein A is a straight chain lower alkylene of 1-7 carbon atoms which may bear one or more lower alkyl substituents, $R_6$ and $R_7$, independently, are hydrogen, lower alkyl, hydroxy-lower alkyl or halo-lower alkyl, or taken together with the nitrogen atom, are a heterocyclic group of 5 or 6 members having up to one other hetero atom which may be sulfur, oxygen or nitrogen, and B is hydrogen, lower alkyl or lower alkanoyl; provided that at least one of $R_2$ or $R_4$ is a radical of the formula

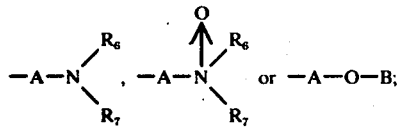

or addition salts thereof with pharmaceutically acceptable acids.

In another aspect, the invention relates to compounds of the formula

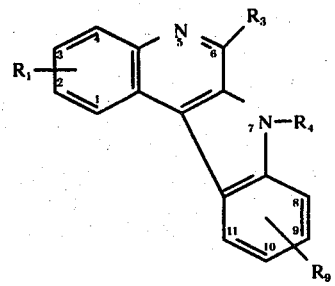

wherein $R_1$ is hydrogen, halogen, trifluoromethyl, lower alkyl, lower alkoxy, amino, cyano or nitro; $R_3$ is hydrogen, halogen, hydrazino, lower alkyl, amino, lower alkylamino, di-lower alkylamino, lower alkoxy, lower alkoxyamino or a radical of the formula

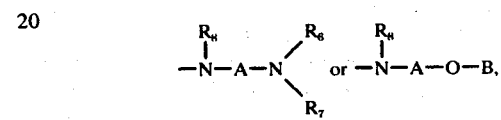

wherein A is a straight chain lower alkylene of 2-7 carbon atoms which may bear one or more lower alkyl substituents, $R_6$ and $R_7$, independently, are hydrogen, lower alkyl, hydroxy-lower alkyl or halo-lower alkyl, or taken together with the nitrogen atom, are a heterocyclic group of 5 or 6 members having up to one other hetero atom which may be sulfur, oxygen or nitrogen, $R_8$ is hydrogen or lower alkyl, and B is hydrogen, lower alkyl or lower alkanoyl; $R_4$ is hydrogen, lower alkyl, lower alkenyl, or a radical of the formula

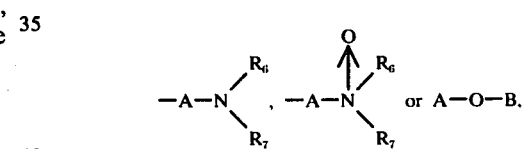

wherein A is a straight chain lower alkylene of 2-7 carbon atoms which may bear one or more lower alkyl substituents, $R_6$ and $R_7$, independently, are hydrogen, lower alkyl, hydroxy-lower alkyl or halo-lower alkyl, or taken together with the nitrogen atom, are a heterocyclic group of 5 or 6 members having up to one other hetero atom which may be sulfur, oxygen or nitrogen, and B is hydrogen, lower alkyl or lower alkanoyl; and $R_9$ is halogen, lower alkyl, lower alkoxy, amino, cyano or nitro; provided that at least one of $R_3$ or $R_4$ is a basic amino side chain or a radical of the formula —A—O—B, or addition salts thereof with pharmaceutically acceptable acids.

DETAILED DESCRIPTION OF THE INVENTION

As used herein, the term "lower alkyl" denotes a straight or branched chain hydrocarbon group containing 1-7 carbon atoms, for example, methyl, ethyl, propyl, isopropyl, butyl, isobutyl, tertiary butyl, neopentyl, pentyl, heptyl, and the like. The term "lower alkoxy" denotes an alkyl ether group in which the alkyl group is as described above, for example, methoxy, ethoxy, propoxy, isopropoxy, butoxy, pentoxy, and the like. The term "lower alkenyl" denotes a straight or branched chain alkenyl of 2 to 7 carbon atoms, for example, vinyl, allyl, butenyl, pentenyl, and the like. The term "halogen" denotes all the halogens; that is, bromine, chlorine, fluorine and iodine; chlorine is preferred. The term "lower alkylene" denotes a straight chain alkylene group of 1 to 7 carbon atoms which may bear one or more lower alkyl substituents such as, for example, methylene, ethylene, propylene, butylene, pentylene, alpha-methyl-methylene, alpha-methyl-ethylene, alpha-methyl-propylene, alpha-methyl-butylene and the like. Preferably, "lower alkylene" is ethylene. The term "basic amino side chain" denotes a radical of the formula

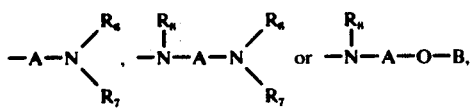

wherein A, $R_6$, $R_7$ and $R_8$ are as defined herein, and includes amino, lower alkoxyamino, mono-lower alkyl-amino and di-lower alkylamino. As used herein, the term "heterocyclic ring of 5 or 6 members" denotes a heterocylic nucleus of 5 or 6 members having up to one hetero atom in addition to the nitrogen of the amino group which may be either nitrogen, oxygen or sulfur, and which may be substituted or unsubstituted, for example, piperidino, piperazino, pyrrolidino, morpholino, imidazoline, 4-lower alkylpiperazino, methylpiperidino, and the like. As used herein, the term "lower alkanoyl" denotes a radical derived from an aliphatic carboxylic acid of 1 to 7 carbon atoms, for example, formyl, acetyl, propionyl and the like.

The invention relates to compounds of the formula

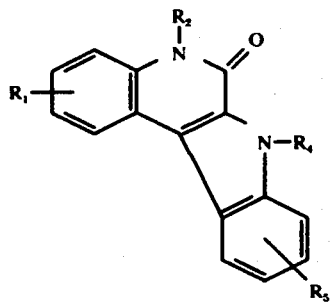

as well as to compounds of the formula

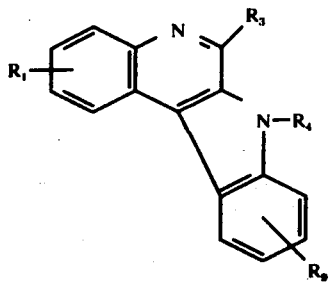

wherein $R_1$ and $R_5$, independently, are hydrogen, halogen, trifluoromethyl, lower alkyl, lower alkoxy, amino, cyano or nitro; $R_2$ and $R_4$, independently, are hydrogen, lower alkyl, cyano-lower alkyl, dihydroxy-lower alkyl, 2,3-epoxy-propyl, lower alkenyl, or a radical of the formula

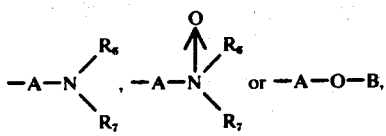

wherein A is a straight chain lower alkylene of 2-7 carbon atoms which may bear one or more lower alkyl substituents, $R_6$ and $R_7$, independently, are hydrogen, lower alkyl, hydroxy-lower alkyl or halo-lower alkyl, or taken together with the nitrogen atom, are a heterocyclic group of 5 or 6 members having up to one other hetero atom which may be sulfur, oxygen or nitrogen, and B is hydrogen, lower alkyl or lower alkanoyl; $R_3$ is hydrogen, halogen, trifluoromethyl, hydrazino, lower alkyl, amino, lower alkylamino, di-lower alkylamino, lower alkoxy, lower alkoxyamino or

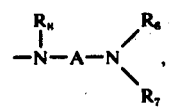

wherein A is a straight chain lower alkylene of 2-7 carbon atoms which may bear one or more lower alkyl substituents, $R_6$ and $R_7$, independently, are hydrogen, lower alkyl, hydroxylower alkyl or halo-lower alkyl, or taken together with the nitrogen atom, are a heterocyclic group of 5 or 6 members having up to one other hetero atom which may be sulfur, oxygen or nitrogen, and $R_8$ is hydrogen or lower alkyl; and $R_9$, independently, is halogen, lower alkyl, lower alkoxy, amino, cyano, or nitro; provided that at least one of $R_2$ or $R_4$ in formula I is a radical of the formula

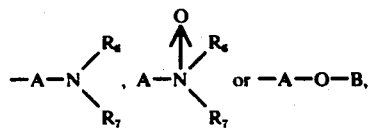

and that at least one of $R_3$ or $R_4$ in formula II is a basic amino side chain or the radical —A—O—B; or addition salts thereof with pharmaceutically acceptable acids.

Exemplary of the compounds of formula I are:
5-(2-dimethylaminoethyl)-7H-indolo[2,3-c]quinolin-6(5H)-one;
5-(2-diethylaminoethyl)-7H-indolo[2,3-c]quinolin-6(5H)-one;
2-chloro-5-(2-dimethylaminoethyl)-7H-indolo[2,3-c]quinolin-6(5H)-one;
2-chloro-5-(2-diethylaminoethyl)-7H-indolo[2,3-c]quinolin-6(5H)-one;
5-(2-dimethylaminoethyl)-2-methyl-7H-indoli[2,3-c]quinolin-6(5H)-one;
5-(2-diethylaminoethyl)-2-methyl-7H-indolo[2,3-c]quinolin-6(5H)-one;
11-chloro-5-(2-dimethylaminoethyl)-7H-indolo[2,3-c]quinolin-6(5H)-one;
7-(2-diethylaminoethyl)-7H-indolo[2,3-c]quinolin-6(5H)-one;
5,7-bis-(2-diethylamino)ethylindolo[2,3-c]quinolin-6(5H)-one;
10-chloro-5-(2-hydroxyethyl)-7H-indolo[2,3-c]quinolin-6(5H)-one;

7-(2-dimethylaminoethyl)-7H-indolo[2,3-c]quinolin-6(5H)-one;

2-chloro-5,7-bis-(2-diethylaminoethyl)-7H-indolo[2,3-c]-quinolin-6(5H)-one dihydrochloride hemihydrate;

10-bromo-2-chloro-5-(2-diethylaminoethyl)-7H-indolo[2,3-c]-quinolin-6(5H)-one hydrobromide;

10-chloro-5-(2-dimethylaminoethyl)-7H-indolo[2,3-c]quinolin-6(5H)-one;

5-(2-dimethylaminoethyl)-10-methoxy-7H-indolo[2,3-c]quinolin-6(5H)-one;

10-chloro-5-(2-methylaminoethyl)-7H-indolo[2,3-c]quinolin-6(5H)-one;

5-(2-aminoethyl)-10-chloro-7H-indolo[2,3-c]quinolin-6(5H)-one;

10-chloro-5-(2-morpholinoethyl)-7H-indolo[2,3-c]quinolin-6(5H)-one;

10-chloro-5-(3-dimethylaminopropyl)-7H-indolo[2,3-c]-quinolin-6(5H)-one;

5-(3-aminopropyl)-10-chloro-7H-indolo[2,3-c]quinolin-6(5H)-one;

10-chloro-5-(3-morpholinopropyl)-7H-indolo[2,3-c]quinolin-6(5H)-one;

5-(2-dimethylaminoethyl)-10-ethyl-7H-indolo[2,3-c]quinolin-6(5H)-one.

5-(2-dimethylaminoethyl)-10-fluoro-7H-indolo[2,3-c]-quinolin-6(5H)-one;

5-(2-dimethylaminoethyl)-10-nitro-7H-indolo[2,3-c]quinolin-6(5H)-one;

8-chloro-5-(2-dimethylaminoethyl)-7H-indolo[2,3-c]quinolin-6(5H)-one;

10-chloro-7H-indolo[2,3-c]quinolin-6(5H)-one;

10-chloro-7-(2-dimethylaminoethyl)-7H-indolo[2,3-c]quinolin-6(5H)-one; and 7-(2-diethylaminoethyl)-5-methyl-7H-indolo[2,3-c]quinolin-6(5H-one.

Exemplary of the compounds of formula II are:

2,6-dichloro-7-(2-diethylaminoethyl)-indolo[2,3-c]quinoline;

2-chloro-6-hydrazino-7H-indolo[2,3-c]quinoline;

6-(2-diethylaminoethylamino)-7-methyl-7H-indolo[2,3-c]-quinoline;

6,10-dichloro-7-(2-diethylaminoethyl)-7H-indolo[2,3-c]-quinoline;

10-chloro-6-(2-diethylaminoethylamino)-7H-indolo[2,3-c]-quinoline;

10-chloro-6-hydrazino-7-(2-diethylaminoethyl)-7H-indolo-[2,3-c]quinoline;

10-chloro-6-amino-7-(2-diethylaminoethyl)-7H-indolo[2,3-c]-quinoline;

10-chloro-7-(2-diethylaminoethyl)-6-methoxyamino-7H-indolo[2,3-c]quinoline, and the like.

Preferred compounds of formula I are characterized by the formula

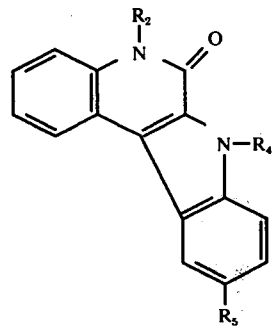

Ia wherein $R_2$ and $R_4$, independently, are hydrogen, lower alkyl, hydroxy-lower alkyl, lower alkoxy-lower alkyl, lower alkenyl or

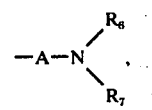

wherein A is a straight chain lower alkylene of 2-7 carbon atoms which may bear one or more lower alkyl substituents, and $R_6$ and $R_7$, independently, are hydrogen or lower alkyl, or taken together with the nitrogen atoms, are a heterocyclic group of 5 or 6 members having up to one other hetero atom which may be sulfur, oxygen or nitrogen; and $R_5$ is nitro, halogen, preferably chlorine, or trifluoromethyl; provided that one of $R_2$ or $R_4$ is the radical

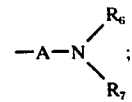

or addition salts thereof with pharmaceutically acceptable acids.

In formula Ia, more preferably one of $R_2$ or $R_4$ is hydrogen or lower alkyl and the other is

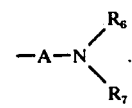

Most preferred compounds of formula Ia are:

10-chloro-5-(2-dimethylaminoethyl)-7H-indolo[2,3-c]quinolin-6(5H)-one;

10-chloro-5-(2-dimethylaminoethyl)-7H-indolo[2,3-c]quinolin-6(5H)-one hydrochloride;

10-chloro-5-(2-methylaminoethyl)-7H-indolo[2,3-c]quinolin-6(5H)-one;

10-chloro-5-(2-aminoethyl)-7H-indolo[2,3-c]quinolin-6(5H)-one; and the like.

Preferred compounds of formula II are characterized by the formula

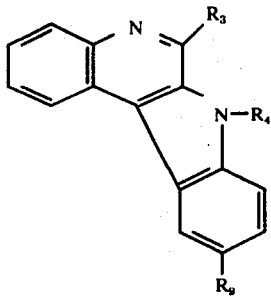

wherein $R_3$ is hydrogen, halogen, trifluoromethyl, hydrazino, lower alkyl, lower alkoxy, lower alkoxyamino or the radical

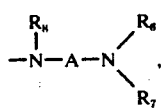

wherein A is a straight chain lower alkylene of 2-7 carbon atoms which may bear one or more lower alkyl substituents, $R_6$ and $R_7$, independently, are hydrogen or lower alkyl, or taken together with the nitrogen atom, are a heterocyclic group of 5 or 6 members having up to one other hetero atom which may be sulfur, oxygen or nitrogen, and $R_8$ is hydrogen or lower alkyl; $R_4$ is hydrogen or the radical

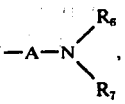

wherein A is a straight chain lower alkylene of 2-7 carbon atoms which may bear one or more lower alkyl substituents, $R_6$ and $R_7$, independently, are hydrogen or lower alkyl, or taken together with the nitrogen atom, are a heterocyclic group of 5 or 6 members having up to one other hetero atom which may be sulfur, oxygen or nitrogen; and $R_9$ is nitro, halogen, preferably chlorine, or trifluoromethyl; provided that one of $R_3$ or $R_4$ is a basic amino side chain as described above; or addition salts thereof with pharmaceutically acceptable acids.

In formula IIa, more preferably, one of $R_3$ or $R_4$ is a basic amino side chain and the other is hydrogen.

Most preferred compounds of formula II are:
6,10-dichloro-7-(2-diethylaminoethyl)-indolo[2,3-c]quinoline;
10-chloro-6-(2-diethylaminoethylamino)-indolo[2,3-c]quinoline; and the like.

The compounds of formulas I and II of the invention can be prepared as hereinafter described in Reaction Schemes I, II and III.

SCHEME I

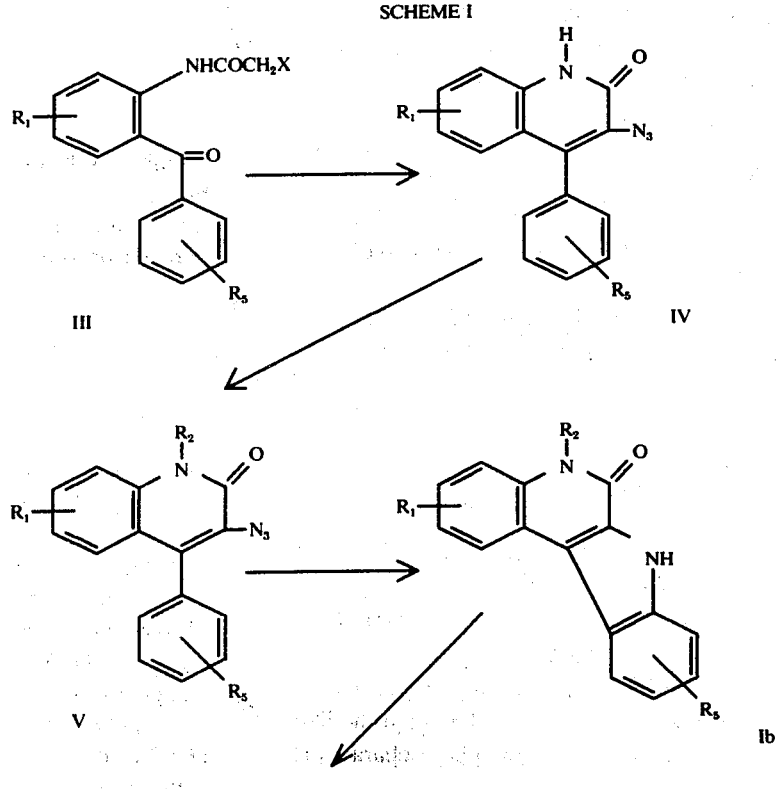

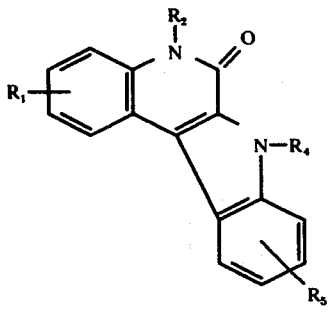

wherein $R_1$, $R_2$, $R_4$ and $R_5$ are as previously described, and X is a leaving group such as halogen, tosyl and the like.

In Reaction Scheme I, the compounds of formula III, which are known compounds or can be prepared in an analogous manner to known compounds, are converted to the compounds of formula IV utilizing an alkaline metal azide such as sodium azide, potassium azide, or the like, in the presence of an inert polar solvent, for example, an alkanol such as methanol, ethanol, propanol or the like, dimethylformamide, dimethylsulfoxide, or the like. Conveniently, the reaction is carried out at a temperature in the range of from about room temperature to 120° C.; preferably, at a temperature in the range of 60°–80° C. Thereafter, the reaction mixture is treated with an alkali metal hydroxide, such as sodium hydroxide or potassium hydroxide, or a quaternary ammonium hydroxide, such as benzyltrimethylammonium hydroxide, at a temperature in the range of from about 0° to about 30°; preferably, the reaction is carried out at room temperature.

Exemplary of the compounds of formula III are:
2'-benzoyl-2-bromo-4'-methylacetanilide;
2'-benzoyl-2-bromo-acetanilide;
2'-benzoyl-4'-chloro-2-iodoacetanilide; and the like.

If desired, a compound of formula IV can be recovered utilizing conventional methods or it can be utilized as such in the next reaction step.

The compounds of formula IV are converted to compounds of formula V, wherein $R_2$ is as hereinbefore described, by treatment with an acid acceptor, such as an alkali metal alkoxide, for example, sodium methoxide, potassium t-butoxide and the like, an alkali metal hydroxide, for example, sodium hydroxide, potassium hydroxide and the like, an alkali metal hydride, for example, sodium hydride, and the like, or alkali amides, for example, sodium amide and the like, and a lower alkylhalide or an amino-lower alkylenehalide of the formula

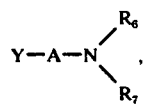

wherein Y is halogen and A, $R_6$ and $R_7$ are as hereinbefore described. It is evident that if $R_2$ is to be hydrogen, no further conversion of the compounds of formula IV is required. Exemplary of the alkylhalides are methyliodide, ethylbromide, propylchloride and the like. Exemplary of the amino-lower alkylenehalides are aminoethylchloride, mono-methylaminoethylchloride, dimethylaminoethylchloride, mono-ethylaminoethylchloride, diethylaminoethylchloride, aminoethylbromide, aminopropylchloride and the like.

The compounds of formula V are cyclized to the compounds of formula Ib by heating to a temperature of from about 100° to about 200°. The conversion is conveniently carried out at the boiling temperature of an inert solvent, for example, a hydrocarbon such as xylene, toluene, mineral oil, and the like, a chlorinated hydrocarbon such as dichlorobenzene, chlorobenzene, trichlorobenzene and the like, or an ether such as diethylether, diglyme, dioxane and the like.

The compounds of formula Ib can be recovered utilizing conventional methods such as crystallization, sublimation or the like.

The compound of formula Ib can be converted to the compounds of formula I wherein $R_4$ is as hereinbefore described, by treatment with an acid acceptor, as hereinbefore described, and a lower alkylhalide, an amino-lower alkylenehalide of the formula

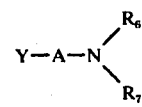

or a halide of the formula Y-A-O-B, wherein Y is halogen and A, B, $R_6$ and $R_7$ are as hereinbefore described. It is evident that if $R_4$ is to be hydrogen, no further conversion of the compounds of formula Ib is required. Exemplary of the alkylhalides are methylchloride, ethylbromide, propylchloride and the like. Exemplary of the amino-lower alkylenehalides are aminoethylchloride, mono-methylaminoethylchloride, dimethylaminoethylchloride, mono-ethylaminoethylchloride, aminoethylbromide, aminopropylchloride and the like. Exemplary of the halides of the formula Y-A-O-B are methoxymethylchloride and the like.

As noted above, a compound of formula I wherein $R_4$ is hydrogen, i.e., a compound of formula Ib in Reaction Scheme I, can be converted to the compound of formula I, wherein $R_4$ is other than hydrogen; therefore, in a similar manner, a compound of formula I, wherein $R_2$ is hydrogen, can be converted into a compound of formula I, wherein $R_2$ is other than hydrogen, by reaction with a suitable halide of the formula $R_2$-Y.

SCHEME II

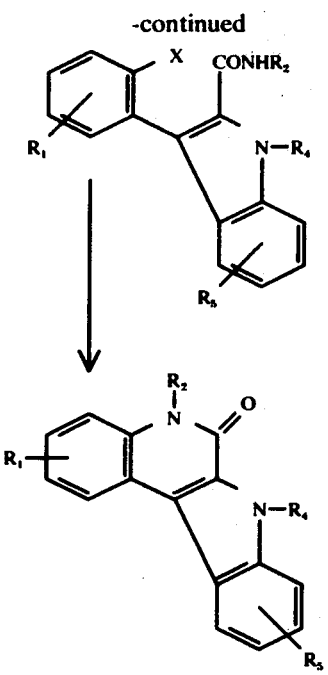

wherein X is a leaving group such as fluorine or the like; $R_1$, $R_2$, $R_4$ and $R_5$ are as hereinbefore described.

In Reaction Scheme II, the compounds of formula VI, which are known compounds or can be prepared in an analogous manner to known compounds, are converted to the compounds of formula I by treatment with a strong base, for example, an alkali metal hydride, such as sodium hydride, at an elevated temperature, for instance, at a temperature in the range of from about 100° to about 200°. Conveniently, the reaction is carried out in the presence of an inert solvent such as dimethylformamide, dimethylsulfoxide, diglyme, hexamethylenephosphoramide and the like.

Exemplary of the compounds of formula VI are:
5-chloro-N-(2-dimethylaminoethyl)-3-(2-fluorophenyl)-indole-2-carboxamide;
N-(2-dimethylaminoethyl)-3-(2-fluorophenyl)-5-methoxyindole-2-carboxamide;
N-(2-dimethylaminoethyl)-3-(2-fluorophenyl)-5-nitroindole-2-carboxamide;
7-chloro-N-(2-dimethylaminoethyl)-3-(2-fluorophenyl)-indole-2-carboxamide, and the like.

wherein $R_1$, $R_4$ and $R_9$ are as hereinbefore described and $R_3'$ is hydrogen, amino, mono-lower alkylamino, di-lower alkylamino, hydrazino, lower alkyl, lower alkoxy, lower alkoxyamino or a radical of the formula $$\begin{array}{cc} R_6 & R_6 \\ | & / \\ N-A-N & \\ & \backslash R_7 \end{array} \quad \text{or} \quad -N-A-O-B,$$

wherein A is a straight chain lower alkylene of 2-7 carbon atoms which may bear one or more lower alkyl substituents, $R_6$ and $R_7$, independently, are hydrogen, lower alkyl, hydroxylower alkyl or halo-lower alkyl, or taken together with the nitrogen atom, are a heterocyclic group of 5 or 6 members having up to one other hetero atom which may be sulfur, oxygen or nitrogen, $R_8$ is hydrogen or lower alkyl, and B is hydrogen, lower alkyl or lower alkanoyl.

In Reaction Scheme III, the 7-indolo[2,3-c]quinolin-6(5H)-ones of formula Ic are converted to the 7H-indolo[2,3-c]-quinolines of formula IIb by treatment with phosphorus pentachloride, phosphorus oxybromide, phosphorus oxychloride, and the like, or combinations thereof. Conveniently, the reaction is carried out with or without solvent. Suitable solvents include inert organic solvents, for example, hydrocarbons, such as toluene, xylene, and the like, chlorinated hydrocarbons, such as chloroform, chlorobenzene, tetrachloroethylene, and the like. The reaction is carried out at a temperature in the range of from about room temperature to about 200°; preferably, at a temperature in the range of 80° to about 150°.

The compounds of formula IIb wherein $R_4$ is —A—OH, can also be prepared from the corresponding compound of formula IIb, wherein $R_4$ is hydrogen, in a known manner, utilizing an alkali metal hydride, such as sodium hydride or the like and a hydroxy-lower alkyl halide.

The compounds of formula IIb wherein $R_4$ is —A—O—B, lower alkyl or a basic amino side chain can also be prepared from the corresponding compound of formula IIb in a known manner utilizing an acid acceptor, as hereinbefore described, and a B—O—A— halide, a lower alkylhalide, a di-lower alkylsulfate, or an amino-lower alkylenehalide of the formula

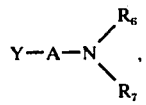

respectively, wherein Y is a halogen and A, B, $R_6$ and $R_7$ are as hereinbefore described.

The compounds of formula IIc can be prepared as follows:

When $R_3'$ is to be hydrogen, the compound of formula IIb, wherein $R_1$ is hydrogen, halogen, lower alkyl, lower alkoxy or amino and $R_9$ is halogen, lower alkyl, lower alkoxy or amino, is treated with a reducing agent, for example, hydrogen and a catalyst such as palladium-on-carbon or Raney nickel, or lithium aluminum hydride, and the like; at a temperature in the range of from about 0° to about 80°. Conveniently, the reduction with lithium aluminum hydride is carried out in the presence of an inert solvent, for example, an ether such as diethylether, tetrahydrofuran, dioxane and the like; the reduction with hydrogen and a catalyst is carried out in the presence of an inert solvent, for example, acetic acid, an alkanol such as methanol, ethanol and the like, or an ether such as diglyme, dioxane and the like.

It is understood that when $R_1$ or $R_9$ above, independently, are an amino group, the latter can be converted to a cyano or a nitro group by the conventional Sandmeyer reaction sequence which involves diazotization followed by treatment with cuprous cyanide.

Alternatively, when $R_3'$ is to be hydrogen, the compound of formula Ic may be reduced with a hydride, for example, lithium aluminum hydride, utilizing the conditions described above, to obtain the corresponding compound of formula IIc.

When $R_3'$ is to be hydrazino, the compound of formula IIb is treated with hydrazine at a temperature in the range of from about 20° to about 150°, with or without solvent.

When $R_3'$ is to be lower alkyl, the compound of formula IIc is treated with a lower alkyl magnesium halide such as methylmagnesium bromide or lower alkyl lithium, such as methyllithium, at a temperature in the range of from about —70° to about 50°. A suitable inert solvent, for example, an ether, such as dioxane and the like, or tetrahydrofuran, can be conveniently utilized.

When $R_3'$ is to be lower alkoxy, the compound of formula IIb is treated with the lower alkoxide of an alkali metal such as sodium, potassium or the like, at a temperature in the range of from about 20° to about 150°. Conveniently, the alkanol corresponding to the lower alkoxide of the alkali metal can be utilized as the solvent. The reaction can be carried out, conveniently, at or above atmospheric pressure.

When $R_3'$ is to be lower alkoxyamino, the compound of formula IIb is treated with a lower alkoxyamine, such as methoxyamine, and the like, in the presence of a solvent, for example, an alkanol such as methanol, ethanol, and the like, dimethylformamide, hexamethylphosphoramide, N-methyl-pyrrolidone, pyridine, and the like, at a temperature in the range of from about 20° to about 150°. The reaction can be carried out, conveniently, at or above atmospheric pressure.

When $R_3'$ is to be a radical of the formula

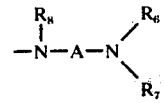

or —N—A—O—B, the compound of formula IIb is treated with a diamine of the formula

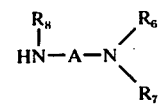

or an amine of the HN—A—O—B, respectively, wherein A, B, $R_6$, $R_7$ and $R_8$ are as hereinbefore described, at an elevated temperature such as a temperature in the range of from about 50° to about 200°. Conveniently, the reaction can be carried out with or without solvent. Suitable solvents comprise dioxane, dimethylsulfoxide, dimethylformamide, hydrocarbons, such as toluene, xylene, or the like.

When $R_3'$ is to be amino, mono-lower alkylamino or di-lower alkylamino, the compound of formula IIb is heated with the appropriate amine under pressure, if necessary.

The compounds of formulas I and II, wherein $R_2$ and $R_4$, independently, are

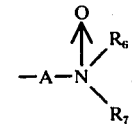

wherein A, $R_6$ and $R_7$ are as described herein, can be prepared from the corresponding desoxy compound by treatment, for example, with m-chloro-perbenzoic acid or the like.

Exemplary of the diamines are:

2-dimethylaminoethylamine;
3-dimethylaminopropylamine;
2-dimethylaminopropylamine;
ethylenediamine;
2-ethylaminoethylamine;
2-(dimethylaminoethyl)-methylamine;
2-morpholinoethylamine; and the like.

Exemplary of the amines are:

hydroxyethylamine;
hydroxypropylamine;
ethoxyethylamine;
methoxyethylamine;
methoxypropylamine;
acetoxyethylamine;
acetoxypropylamine; and the like.

SCHEME IV

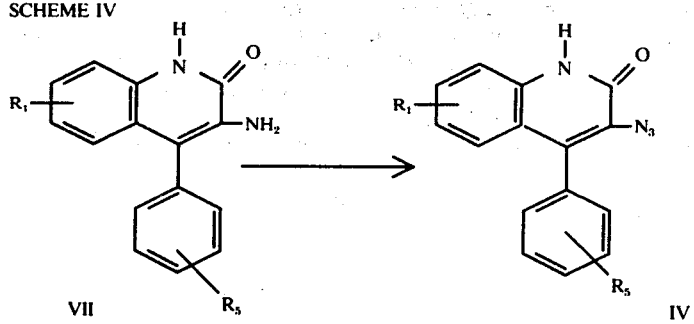

VII → IV wherein $R_1$, $R_3$ and $R_5$ are as hereinbefore described.

In Reaction Scheme Iv, the compounds of formula VII, which are known compounds or can be prepared in an analogous manner to known compounds, are converted to the compounds of formula IV by diazotization with nitrous acid using sulfuric acid as a solvent and subsequently treating the diazonium salt with an alkali metal azide, such as sodium azide, potassium azide and the like, at a temperature in the range of from about −20° to about 20°. Thereafter, the compounds of formula IV can be recovered by conventional methods such as crystallization, chromatography, or the like.

The compounds of formula I, wherein $R_2$ is hydrogen, are tautomeric. Such tautomers are within the scope of the invention and are characterized by the formulas

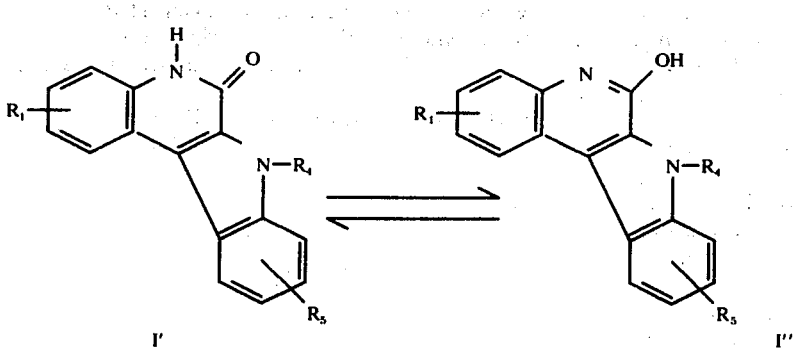

I' ⇌ I'' wherein $R_4$, $R_5$ and $R_6$ are as previously described.

The compounds of formulas I and II, which bear a basic amino side chain, form addition salts with pharmaceutically acceptable organic or inorganic acids such as hydrohalides, e.g., hydrochloride, hydrobromide, hydroiodide, other mineral acid salts such as sulfate, nitrate, phosphate and the like, alkyl- and mono-arylsulfonates such as ethanesulfonate, toluenesulfonate, benzenesulfonate, or the like, other organic acid salts such as acetate, tartrate, maleate, citrate, benzoate, salicylate, ascorbate and the like.

Non-pharmaceutically acceptable acid addition salts of the compounds of formulas I and II above can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable anion.

The compounds of formulas I and II and their pharmaceutically acceptable salts are useful as antitumor agents. Thus, they inhibit the growth of transplantable tumors, for example, Sarcoma 180 (S-180), in mice and rats. The useful inhibitory activity of the compounds of formulas I and II against transplantable tumors can be demonstrated in warm-blooded animals. For example, mice are weighed and divided into groups of eight animals for each drug and control group. Small pieces of S-180 tumors are implanted by trocar subcutaneously on the ventral surface of the mouse. Mice are treated i.p. with 2/5 of the maximum tolerated dose immediately after implantation and then once daily until eight treatments are given. The mice are weighed and sacrificed 8 days after implantation. The weight of each excised tumor is determined in mg. and averaged for each group of eight mice. The total body weight gain or loss for the treated period is recorded. The average tumor weight of the untreated controls (C) is divided by the average tumor weight of each treated group (T). The results are expressed as C/T ratio. If a ratio greater than 2 is observed, the compound is active.

When 10-chloro-5-(2-dimethylaminoethyl)-7H-indolo[2,3-c]-quinolin-6(5H)-one, which has demonstrated an acute $LD_{50}$ in mice of >2000 mg/kg. i.p. and >4000 mg/kg. p.o. is used as the test substance, the C/T ratio is 3.50 and 3.05 at 100 mg/kg. i.p. or orally, respectively, administered once daily for 8 days.

The compounds of formulas I and II and salts thereof as herein described, can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkylene glycols, and the like. The pharmaceutical preparations can be employed in a solid form, for example, as tablets, troches, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The compounds of the invention, when A in formulas I and II possesses an asymmetric carbon atom, are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture with an optically active resolving agent, for example, an optically active acid, such as d-10-camphorsulfonic acid, which can be reacted with the amino group. The formed diastereomers are separated by selective crystallization and converted to the corresponding optical isomer. Thus, the invention covers the racemates of the compounds of formulas I and II as well as their optically active isomers.

The following examples further illustrate the invention. All parts are by weight and all temperatures are in degrees Centigrade, unless otherwise mentioned.

EXAMPLE 1

Preparation of 3-azido-4-phenylcarbostyril

To a hot solution of 98.5 g. of 2'-benzoyl-2-bromoacetanilide in 2 1. methanol was added in one portion 39.0 g. of sodium azide. The mixture was heated to a slow reflux on a steam bath for 20 minutes. As the mixture cooled partially to room temperature, 18 ml. of benzyltrimethylammonium hydroxide (35% methanolic solution) was added. After standing overnight at room temperature, the orange-yellow needles that formed were collected, washed with methanol and dried at 60° C.; yield 76.6 g. (94%) of 3-azido-4-phenylcarbostyril, having a melting point of 120°–140° dec. to high melting solid.

EXAMPLE 2

Preparation of 3-azido-6-chloro-4-phenylcarbostyril

A solution of 120 g. of 2'-benzoyl-4'-chloro-2-iodoacetanilide (mp 125°–127°) and 39.0 g. of sodium azide in 3.2 1. of methanol was heated to reflux for 15 minutes. The mixture was allowed to cool at room temperature. A methanolic solution of benzyltrimethylammonium hydroxide (35% concentration, 25 ml.) was added while the mixture was still warm. After standing overnight, 70.5 g. (79%) of 3-azido-6-chloro-4-phenylcarbostyril, as yellow needles, were collected and washed with methanol, melting point was indefinite because of decomposition in the range of 120°–150°, forming high-melting indoloquinoline. An analytical sample was obtained by recrystallization from methanol.

Alternately, 2'-benzoyl-4'-chloro-2-bromoacetanilide can be used in the same manner giving comparable yields of 3-azido-6-chloro-4-phenylcarbostyril.

EXAMPLE 3

Preparation of 2-azido-6-methyl-4-phenylcarbostyril

To a warm solution of 5.00 g. of 2'-benzoyl-2-bromo-4'-methylacetanilide in 75 ml. of methanol was added 2.0 g. of sodium azide. The solution was heated to reflux for 15 minutes. On partial cooling, 0.84 ml. of a 35% solution of benzyltrimethylammonium hydroxide in methanol was added. On standing at room temperature for 2 hours, 3.5 g. (81%) of analytically pure 2-azido-6-methyl-4-phenylcarbostyril crystallized as yellow needles, having a melting point of 140° dec. It was collected and washed with methanol.

EXAMPLE 4

Preparation of 7H-indolo[2,3-c]quinolin-6(5H)-one a. From hydrogenolysis of the chloro analog, i.e., 2-chloro-7H-indolo[2,3-c]quinolin-6(5H)-one A solution of 1.00 g. of 2-chloro-7H-indolo [2,3-c]quinolin-6(5H)-one in 400 ml. of ethanol containing 1.0 g. of 10% palladium on carbon as catalyst was hydrogenated at room temperature under 1 atmosphere of hydrogen. Hydrogen uptake was rapid and stopped after 35 minutes. The catalyst was removed by filtration. Evaporation of ethanol yielded an almost colorless amorphous solid residue which on collection and washing with ethanol yielded 634 mg. of 7H-indolo[2,3-c]quinolin-6(5H)-one, having a melting point of 295°–305°. After two recrystallizations from pyridine, 237 mg. of colorless prismatic needles of 7H-indolo[2,3-c]-quinolin-6(5H)-one were obtained, having a melting point of 312°–314°.

b. From pyrolysis of 3-azido-4-phenylcarbostyril

A suspension of 114 g. of 3-azido-4-phenylcarbostyril in 2 1. of toluene was heated to reflux until nitrogen evolution ceased (5 hours). On cooling, 7H-indolo[2,3-c]quinolin-6(5H)-one crystallized; 84.7 g. (84 percent), having a melting point of 314°–316°.

EXAMPLE 5

Preparation of 2-chloro-7H-indolo[2,3-c]quinolin-6(5H)-one

A suspension of 128 g. of 3-azido-6-chloro-4-phenylcarbostyril in 3 1. of toluene was heated to reflux for 5 hours. On cooling, 113 g. (98 percent) of analytically pure 2-chloro-7H-indolo[2,3-c]quinolin-6(5H)-one crystallized from solution as colorless needles, having a melting point of 325°–327° (change in crystal form in the range of 270°–290°; melts with sublimation).

EXAMPLE 6

Preparation of 3-azido-4-(2-chlorophenyl)carbostyril

To a warm solution of 5.0 g. of 2-bromo-2'-(2-chlorobenzoyl)acetanilide in 100 ml. of methanol was added 1.8 g. of sodium azide. The solution was heated to reflux for 15 minutes. On addition of 0.77 ml. of a 35 percent solution of benzyltrimethylammonium hydroxide in methanol, and standing at room temperature overnight, 1.8 g. of pure (tlc) 3-azido-4-(2-chlorophenyl)carbostyril crystallized and was collected and washed with methanol. On recrystallization from dimethylformamide-methanol, pale yellow needles were obtained, having a melting point of 152°–155° dec.

EXAMPLE 7

Preparation of 3-azido-4-(2-fluorophenyl)-6-nitrocarbostyril

To a solution of 29.9 g. of 3-amino-4-(2-fluorophenyl)-6-nitrocarbostyril in 200 ml. of concentrated sulfuric acid, maintained at 0° with an ice bath, was added in portions, 8.28 g. of sodium nitrite. After stirring at 0° for 15 minutes, the mixture was poured carefully into a swirling mixture of ice and water in which 15.6 of sodium azide was dissolved. More ice was added as needed to keep the mixture cold. The suspension was allowed to stand at room temperature until the foaming subsided. The amorphous yellow solid was collected and washed thoroughly with water to yield 35.7 g. of 3-azido-4-(2-fluorophenyl)-6-nitrocarbostyril, indefinite decomposition temperature at about 140°. On recrystallization from dimethyl-formamide-methanol, yellow prisms of 3-azido-4-(2-fluorophenyl)-6-nitrocarbostyril were obtained.

EXAMPLE 8

Preparation of
11-fluoro-2-nitro-7H-indolo[2,3-c]quinolin-6(5H)-one

A suspension of 37.0 g. of 3-azido-4-(2-fluorophenyl)-6-nitrocarbostyril in 800 ml. of toluene was heated to reflux for 5 hours. The crystalline precipitate formed was collected: 31.7 g. Recrystallization from dimethylformamide afforded 20.2 g. (65 percent) of yellow needles of 11-fluoro-2-nitro-7H-indolo[2,3-c]quinolin-6(5H)-one, having a melting point of >350°.

EXAMPLE 9

Preparation of
5-(2-dimethylaminoethyl)-7H-indolo[2,3-c]quinolin-6(5H)-one

A mixture of 26.2 g. of 3-azido-4-phenylcarbostyril, 12.00 g. of sodium hydride (50 percent dispersion in oil) and 1.0 l. of dimethylformamide was stirred for 0.5 hour. To this was added 14.4 g. of 2-chloro-N,N-dimethylethylamine hydrochloride and the mixture was stirred at 60° for 3 hours.

On cooling, the excess hydride was decomposed with water. The solvent was removed by evaporation in vacuo. The residue was partitioned between methylene chloride and water. The methylene chloride layer was dried and evaporated to dryness. The residual oil was dissolved in 1.0 l. of toluene, and the mixture was heated under reflux for 3 hours.

On cooling, light yellow needles of 5-(2-dimethylaminoethyl)-7H-indolo [2,3-c]quinolin-6(5H)-one were collected, washed with toluene, hexane. The light yellow needles were recrystallized from dimethylformamide-methanol to give 15.00 g. (50 percent) of colorless needles of 5-(2-dimethylaminoethyl)-7H-indolo [2,3-c]quinolin-6(5H)-one, having a melting point of 261°-263°.

EXAMPLE 10

Preparation of
5-(2-diethylaminoethyl)-7H-indolo[2,3-c]quinolin-6(5H)-one

A mixture of 26.2 g. of 3-azido-4-phenylcarbostyril, 7.2 g. of NaH (50 percent dispersion in oil), and 1.0 l. of dimethylformamide was stirred for 0.5 hour. To this solution was added 50 ml. of 2-chloro-N,N-diethylethylamine (3.2 M in toluene) and the mixture was stirred for 3 hours.

The excess hydride was decomposed with water. Solvent was removed by evaporation in vacuo. The residue was partitioned between methylene chloride and water. The methylene chloride layer was dried and evaporated to dryness. The residual oil was dissolved in 300 ml. of toluene, and the mixture was heated under reflux for 2 hours.

On cooling, the light yellow amorphous solid was collected, which washed with toluene, then hexane, gave 25.5 g. (78 percent) of 5-(2-diethylaminoethyl)-7H-indolo[2,3-c]quinolin-6(5H)-one, having a melting point of 238°-240°.

An analytical sample was prepared by recrystallization from dimethylformamide/methanol to give 15.5 g. (50 percent) of 5-(2-diethylaminoethyl)-7H-indolo[2,3-c]quinolin-6(5H)-one, having a melting point of 235°-238° as colorless needles.

EXAMPLE 11

Preparation of
2-chloro-5-(2-dimethylaminoethyl)-7H-indolo-[2,3-c]quinolin-6(5H)-one A mixture of 5.92 g. of 3-azido-6-chloro-4-phenylcarbostyril, 1.20 g. of NaH (50 percent dispersion in oil), and 100 ml. of dimethylformamide was stirred for 0.5 hour. To this was added 7.5 ml. of 2-chloro-N,N-dimethylethylamine (3.0 M in benzene), and the mixture was heated at 60° with stirring overnight (15 hours).

On cooling, the mixture was acidified with 1 N HCl, then diluted with cold water. The precipitated azide was collected, washed with water. The solids were suspended in water, neutralized with saturated aqueous NaHCO$_3$ and extracted with methylene chloride. The methylene chloride layer was dried and evaporated to dryness, and the residue was dissolved in 200 ml. of toluene. This solution was heated under reflux for 5 hours. On cooling, the amorphous solid formed, was collected and washed with toluene. Recrystallization from dimethylformamide/methanol gave 3.2 g. (32 percent) of 2-chloro-5-(2-dimethylaminoethyl)-7H-indolo[2,3-c]quinolin-6(5H)-one, having a melting point of 277°-279° as colorless needles.

EXAMPLE 12

Preparation of
2-chloro-5-(2-diethylaminoethyl)-7H-indolo-[2,3-c]quinolin-6(5H)-one A mixture of 74.00 g. of 3-azido-6-chloro-4-phenylcarbostyril, 15.3 g. of NaH (50 percent dispersion in oil), and 1.25 l. of dimethylformamide was stirred for 0.5 hour. To this was added 100 ml. of diethylaminoethyl chloride 3.2 M in toluene and the mixture was stirred for 2 hours.

The reaction mixture was neutralized with 1 N HCl (about 800 ml.). The light yellow amorphous solid formed was collected and recrystallized from ethanol-water to give 100.0 g. of light yellow flakes.

These flakes were suspended in water, neutralized with saturated sodium bicarbonate, extracted with methylene chloride. The methylene chloride layer was washed with water, dried and evaporated to dryness. The residual oil was dissolved in 500 ml. of toluene, heated under reflux for 2 hours.

On cooling, the product precipitated out of solution and was collected and washed with toluene and hexane. The amorphous solid was recrystallized from dimethylformamide/methanol yielding 39.20 g. (43 percent) of 2-chloro-5-(2-diethylaminoethyl)-7H-indolo [2,3-c]quinolin-6(5H)-one as colorless needles, having a melting point of 281°-283°.

EXAMPLE 13

Preparation of 5-(2-dimethylaminoethyl)-2-methyl-7H-indolo[2,3-c]quinolin-6(5H)-one A mixture of 23.00 g. of 3-azido-4-phenyl-6-methylcarbostyril, 14.5 g. of sodium hydride (50 percent in mineral oil), and 1.0 l. of dimethylformamide was stirred for 30 minutes. To this mixture was added 21.60 g. of 2-chloro-N,N-dimethylethylamine hydrochloride and stirring continued at 60° C. for 3 hours.

On cooling, the excess hydride was decomposed with water. The dimethylformamide was removed in vacuo. The residue was partitioned between methylene chloride and water. The methylene chloride layer was dried and evaporated to dryness.

The obtained residue was dissolved in 1.0 l. of toluene, and was heated under reflux for 2 hours. On cooling, the resulting crystalline product was collected, washed with hexane to yield 9.2 g. (35 percent) of 5-(2-dimethylaminoethyl)-2-methyl-7H-indolo [2,3-c]quinolin-6(5H)-one, having a melting point of 277°–279°.

An analytical sample was prepared by recrystallization from dimethylformamide as colorless needles, having a melting point of 276°–278°.

EXAMPLE 14

Preparation of 5-(2-diethylaminoethyl)-2-methyl-7H-indolo[2,3-c]quinolin-6(5H)-one A mixture of 5.4 g. of 3-azido-4-phenyl-6-methylcarbostyril, 1.45 g. of sodium hydride (50 percent dispersion in mineral oil) and 200 ml. of dimethylformamide was stirred for 0.5 hour at room temperature. To this mixture was added 10 ml. of 2-chloro-N,N-diethylethylamine (2.8 M in toluene), and the mixture was stirred at room temperature for 1 hour.

The hydride was decomposed with water. The solvent was removed in vacuo and the residue partitioned between methylene chloride and water. The methylene chloride layer was dried and evaporated to dryness. The residual oil was dissolved in 1.0 l. of toluene and heated under reflux for 2 hours. On cooling, fibrous colorless needles were obtained. These were collected, washed with toluene, then hexane, and yielded 4.2 g. (62 percent) of 5-(2-diethylaminoethyl)-2-methyl-7H-indolo[2,3-c] quinolin-6(5H)-one, having a melting point of 281°–284°. An analytical sample was prepared by recrystallization from dimethylformamide/acetonitrile.

EXAMPLE 15

Preparation of 11-chloro-5-(2-dimethylaminoethyl)-7H-indolo-[2,3-c]quinolin-6(5H)-one A mixture of 29.6 g. of 3-azido-4-0-dichlorophenylcarbostyril, 14.5 g. of sodium hydride (50 percent in mineral oil) and 1.0 l. of dimethylformamide was stirred for 30 minutes. To this was added 21.6 g. of 2-chloro-N,N-dimethylethylamine hydrochloride, and the resulting mixture was heated to 60° C. for 2 hours.

On cooling, the excess hydride was decomposed with water, and the dimethylformamide was removed in vacuo. The residual oil was partitioned between methylene chloride and water, and the methylene chloride layer was dried and evaporated.

The residual oil was dissolved in 500 ml. of toluene, and the mixture heated under reflux for 3 hours. On cooling, 3.0 g. (9 percent) of 11-chloro-5-(2-dimethylaminoethyl)-7H-indolo[2,3-c]quinolin-6(5H)-one as colorless needles were collected. An analytical sample was prepared by recrystallization from dimethylformamide/acetonitrile, had a melting point of 276°–277°.

EXAMPLE 16

Preparation of 2,6-dichloro-7H-indolo[2,3-c]quinoline

A suspension of 60 g. of 2-chloro-7H-indolo[2,3-c]quinolin-6(5H)-one in 950 ml. of phosphorous oxychloride was heated under nitrogen on a steam bath for 2 hours. The deep yellow granular complex that formed was collected and washed thoroughly with anhydrous ether (85.5 g.). After drying, this complex was suspended in 500 ml. of water to which 300 ml. of concentrated aqueous ammonium hydroxide solution was added, in portions, with stirring. The resulting pale yellow solid was collected and washed with water. After recrystallization from 2 l. of acetonitrile, 37.5 g. (68 percent) of colorless needles of 2,6-dichloro-7H-indolo[2,3-c]quinoline was obtained, which had a melting point of 262°–264°. Recrystallizations from acetonitrile afforded an analytical sample, melting point 265°–266°.

EXAMPLE 17

Preparation of 2,6-dichloro-7-methylindolo[2,3-c]quinoline

To a solution of 14.3 g. of 2,6-dichloro-7H-indolo[2,3-c]-quinoline in 500 ml. of tetrahydrofuran was added 2.5 g. of a 57 percent dispersion of sodium hydride in oil and 5.0 ml. of dimethylsulfate. The mixture was stirred at room temperature overnight. The initially clear solution soon deposited the product as a colorless amorphous precipitate. The solid was collected and washed with water and tetrahydrofuran. After recrystallizations from acetonitrile, 14.5 g. (98 percent) colorless fibrous needles of 2,6-dichloro-7-methylindolo[2,3-c]-quinoline were obtained, which had a melting point of 226°–227°.

EXAMPLE 18

Preparation of 7-(2-diethylaminoethyl)-7H-indolo[2,3-c]quinolin6(5H)-one and 5,7-bis-(2-diethylamino)ethylindolo[2,3-c]-quinolin-6(5H)-one dihydrochloride To a suspension of 30.0 g. of 7H-indolo[2,3-c]quinolin-6(5H)one in 1000 ml. of dimethylformamide was added to 10.0 g. of sodium hydride (50 percent dispersion in oil). The mixture was stirred at room temperature for 15 minutes and to this mixture was added 100 ml. of a solution of diethylaminoethyl chloride (43 percent by weight, in toluene). The mixture was stirred at room temperature for 20 hours and thereafter diluted with 2000 ml. of water and extracted into methylene chloride. The methylene chloride layer was dried over sodium sulfate and evaporated. The residue was treated with ethanol. The ethanol insolubles were removed by filtration. The remaining amorphous solid obtained was crystallized from dimethylformamide/ethanol to give 6.0 g. (14 percent) of 7-(2-diethylaminoethyl)-7H-indolo[2,3-c]quinolin-6(5H)-one, having a melting point of 237°–240° as colorless fibrous needles.

The ethanolic mother liquor was evaporated to dryness. The residual oil was redissolved in a minimum amount of ethanol, then treated with a 4 M solution of HCl in ethanol. The colorless crystalline salt that precipitated was collected and washed with ethanol. After recrystallization from ethanol, 30.0 g. (56 percent) of 5,7-bis-(2-diethylamino)ethylindolo-[2,3-c]quinolin-6(5H)-one dihydrochloride was obtained as colorless fibrous needles, having a melting point of 280°–282°. Further recrystallizations raised the melting point to 288°–290°.

EXAMPLE 19

Preparation of 7-(2-dimethylaminoethyl)-7H-indolo[2,3-c]quinolin-6(5H)-one

To a suspension of 10.0 g. of 7H-indolo[2,3-c]quinolin6(5H)-one and 2.4 g. of sodium hydride (57 percent dispersion in oil) in 150 ml. of dry tetrahydrofuran was added 50 ml. of a toluene solution containing 126 mmoles of 2-dimethylaminoethyl chloride. The mixture was stirred and heated under nitrogen at 60° for 15 hours. After cooling, the mixture was diluted with 200 ml. of water. The organic layer was washed once with water, dried over anhydrous sodium sulfate and evaporated to dryness. The residual solid on recrystallizations from ethanol yielded 2.5 g. (19 percent) of 7-(2-dimethylaminoethyl)-7H-indolo[2,3-c]quinolin-6(5H)-one as colorless needles, having a melting point of 259°–260°.

EXAMPLE 20

Preparation of 2-chloro-5,7-bis-(2-diethylaminoethyl)-7H-indolo-[2,3-c]quinolin-6(5H)-one dihydrochloride hemihydrate To a suspension of 30.0 g. of 2-chloro-7H-indolo[2,3-c]-quinolin-6(5H)-one in 1500 ml. of dimethylformamide was added 12.0 g. of sodium hydride (50 percent dispersion in oil). The mixture was stirred at room temperature for 0.5 hour and to this mixture was added 140 ml. of a 2.8 M solution of diethylaminoethyl chloride in toluene. The reaction mixture was stirred for 2 hours, and thereafter the excess hydride was decomposed (~ 100 ml. of water). The dimethylformamide was evaporated in vacuo, and the residue was partitioned between methylene chloride and water. The methylene chloride layer was dried over anhydrous sodium sulfate and evaporated to dryness. The residue was dissolved in a minimum of ethanol (400 ml.) and to this was added 200 ml. of 4.0 M ethanolic HCl. The mixture was evaporated to dryness in vacuo, and the residue on crystallization from isopropanol, gave 38.6 g. (65 percent) of 2-chloro-5,7-bis-(2-diethylaminoethyl)-7H-indolo[2,3-c]quinolin-6(5H)-one dihydrochloride hemihydrate, as fibrous needles having a melting point of 261°–264° dec.

EXAMPLE 21

Preparation of 10-bromo-2-chloro-7H-indolo[2,3-c]quinolin-6(5H)-one

To a suspension of 26.8 g. of 2-chloro-7H-indolo[2,3-c]-quinolin-6(5H)-one in 2.5 l. of acetic acid was added 16.00 g. of bromine in acetic acid. The mixture was heated under reflux for 5 hours.

On cooling, the light yellow amorphous solid formed was collected and washed with acetic acid. Recrystallization from dimethylformamide-CH$_3$OH yielded 27.00 g. (78 percent) of 10-bromo-2-chloro-7H-indolo[2,3-c]quinolin-6(5H)-one as colorless needles, having a melting point of >350°.

EXAMPLE 22

Preparation of 10-bromo-2-chloro-5-(2-diethylaminoethyl)-7H-indolo[2,3-c]quinolin-6(5H)-one hydrobromide To a solution of 9.2 g. of 2-chloro-5-(2-diethylaminoethyl)-7H-indolo[2,3-c]quinolin-6(5H)-one in 100 ml. of acetic acid was added dropwise 6.00 g. of bromine in 150 ml. of acetic acid. The precipitated yellow amorphous solid was collected and washed with acetic acid and upon crystallization from acetonitrile gave 9.2 g. (82 percent) of crude 10-bromo-2-chloro-5-(2-diethylaminoethyl)-7H-indolo[2,3-c]quinolin-6(5H)-one hydrobromide, having a melting point of 295°–298°.

Purification by crystallization from dimethylformamide/ether gave 6.3 g.(49%) of 10-bromo-2-chloro-5-(2-diethylaminoethyl)-7H-indolo[2,3-c]quinolin-6(5H)-one hydrobromide as colorless needles having a melting point of 304°–306° dec.

EXAMPLE 23

Preparation of ethyl 5-chloro-3-(2-fluorophenyl)indole-2-carboxylate

A solution of 60 g. of sodium hydroxide in 125 ml. of water was added to a solution of 119 g. of ethyl 2-acetyl-3-(2-fluorophenyl)propionate in 500 ml. of ethanol cooled to −20°. While the temperature was maintained at −5°, a diazonium salt solution prepared from 64 g. of p-chloroaniline, 200 ml. of concentrated hydrochloric acid, 300 ml. of water and 35 g. of sodium nitrite was added with stirring. After complete addition, the mixture was stirred for 1 hour without cooling. The heavy, red oil which formed was extracted with benzene. The extracts were dreid over sodium sulfate and evaporated. The remaining red oil was dissolved in 1 l. of ethanol containing 7.5 percent hydrogen chloride. After refluxing for 16 hours, the reaction mixture was diluted with 500 ml. of water and cooled with ice. The separated crystals were collected, washed with water and recrystallized from ethanol to yield 84 g. (53 percent) of ethyl 5-chloro-3-(2-fluorophenyl)indole-2-carboxylate, having a melting point of 189°–191°.The analytical sample was recrystallized from methylene chloride/ethanol, mp 191°–193°.

EXAMPLE 24

Preparation of ethyl 3-(2-fluorophenyl)-5-methoxyindole-2-carboxylate

The reaction of the diazonium salt prepared from 24.6 g. of p-anisidine with the sodium salt of 47.6 g. of ethyl 2-acetyl-3-(2-fluorophenyl)propionate as described above, gave the required hydrazone as a red o.i. This was converted to the indole by refluxing for 4 hours in 240 ml. of ethanol containing 7.5 percent of hydrogen chloride. The product, crystallized by the addition of 200 ml. of water was collected, washed with water and recrystallized from ethanol to yield 26.5 g. (42 percent) of ethyl 3-(2-fluorophenyl)-5-methoxyindole-2-carboxylate, having a melting point of 138°–142°. The analytical sample was prepared by recrystallization from methylene chloride/hexane and had a mp of 142°–144°.

EXAMPLE 25

Preparation of 5-chloro-3-(2-fluorophenyl)indole-2-carboxylic acid

A mixture of 32 g. of ethyl 5-chloro-3-(2-fluorophenyl)-indole-2-carboxylate, 12.3 g. of potassium hydroxide, 300 ml. of ethanol and 30 ml. of water was refluxed for 1 hour. The crystals which precipitated upon acidification with dilute hydrocloric acid were collected, washed with water and dried to yield 27 g. (93 percent) of 5-chloro-3-(2-fluorophenyl)indole-2-carboxylic acid, having a melting point of 245°–248°. A sample recrystallized from ethanol/water was analyzed and had a mp of 257°–259°.

EXAMPLE 26

Preparation of 3-(2-fluorophenyl)-5-methoxyindole-2-carboxylic acid

The saponification of 15.6 g. of ethyl 3-(2-fluorophenyl)-5-methoxyindole-2-carboxylate with 6.2 g. of potassium hydroxide in 150 ml. of ethanol and 15 ml. of water was carried out as described above to yield 13.5 g. (94 percent) of 3-(2-fluorophenyl)-5-methoxyindole-2-carboxylic acid, having a melting point of 206°–208° after recrystallization from ether.

EXAMPLE 27

Preparation of N-ethyl-5-chloro-3-(2-fluorophenyl)indole-2-carboxamide

A mixture of 11.6 g. of 5-chloro-3-(2-fluorophenyl)indole-2-carboxylic acid and 75 ml. of thionyl chloride was refluxed for 2 hours. The thionyl chloride was evaporated under reduced pressure and finally removed azeotropically with benzene. The solid residue was boiled in 200 ml. of methylene chloride. The insoluble material was separated by filtration and the filtrate was added to a stirred solution of 25 g. of 70 percent ethylamine in water in 100 ml. of ethanol. After stirring for 10 minutes, the reaction mixture was diluted with water. The methylene chloride layer was separated, dried over sodium sulfate and evaporated. Crystallization of the residue from chloroform yielded 8.7 g. (68 percent) of N-ethyl-5-chloro-3-(2-fluorophenyl)indole-2-carboxamide, having a melting point of 243°–245°. The analytical sample was recrystallized from methylene chloride/ethyl acetate and had a melting point of 248°–250°.

EXAMPLE 28

Preparation of 5-chloro-N-(2-dimethylaminoethyl)-3-(2-fluorophenyl)indole-2-carboxamide A solution of the acid chloride in methylene chloride was prepared as described in previous examples from 29 g. of 5-chloro-3-(2-fluorophenyl)indole-2-carboxylic acid and 250 ml. of thionyl chloride. It was added to a stirred solution of 50 ml. of (2-dimethylamino)ethylamine in 200 ml. of methylene chloride. After stirring for 10 minutes, the methylene chloride was washed with 10 percent aqueous sodium carbonate and water, dried over sodium sulfate and evaporated. The remaining crystals were slurried with ether and collected to yield 25 g. (69 percent) of 5-chloro-N-(2-dimethylaminoethyl)-3-(2-fluorophenyl)indole-2-carboxamide, having a melting point of 229°–231°. For analysis, it was recrystallized from benzene/ethanol and had a melting point of 234°–236°.

EXAMPLE 29

Preparation of N-(2-dimethylaminoethyl)-3-(2-fluorophenyl)-5-methoxyindole-2-carboxamide In an analogous manner to the previous example, 14.3 g. of 3-(2-fluorophenyl)-5-methoxyindole-2-carboxylic acid was reacted with 75 ml. of thionyl chloride and subsequently with 25 ml. of 2-dimethylaminoethylamine in 100 ml. of methylene chloride to yield 11 g. (62 percent) of N-(2-dimethylaminoethyl)3-(2-fluorophenyl)-5-methoxyindole-2-carboxamide, having a melting point of 184°–186° after recrystallization from ethanol.

EXAMPLE 30

Preparation of 10-chloro-5-ethyl-7H-indolo[2,3-c]quinolin-6(5H)-one

A mixture of 3.2 g. of N-ethyl-5-chloro-3-(2-fluorophenyl)-indole-2-carboxamide, 1 g. of sodium hydride suspension (50 percent in mineral oil) and 40 ml. of dimethylformamide was heated to reflux for 10 minutes with stirring in an atmosphere of nitrogen. The cooled reaction mixture was poured into water. The precipitated crystals were collected, washed with water and recrystallized from dimethylformamide to leave 2.5 g. (84 percent) of 10-chloro-5-ethyl-7H-indolo[2,3-c]quinolin-6(5H)-one, having a melting point of 320°–325°.

EXAMPLE 31

Preparation of 10-chloro-5-(2-dimethylaminoethyl)-7H-indolo-[2,3-c]quinolin-6(5H)-one 15 g. of sodium hydride suspension (50 percent in mineral oil) was washed with hexane and added in portions to a solution of 36 g. of 5-chloro-N-(2-dimethylaminoethyl)-3-(2-fluorophenyl)-indole-2-carboxamide in 400 ml. of dimethylformamide. After complete addition, the mixture was heated to reflux for 10 minutes with stirring under nitrogen. The cooled solution was then poured into 2 liters of ice/water. The precipitate was collected, washed with water and recrystallized from boiling dimethylformamide to yield 29.6 g. (87 percent) of 10-chloro-5-(2-dimethylaminoethyl)-7H-indolo[2,3-c]quinolin-6(5H)-one, having a melting point of 295°–298°.

EXAMPLE 32

Preparation of 5-(2-dimethylaminoethyl)-10-methoxy-7H-indolo-[2,3-c]quinolin-6(5H)-one In an analogous manner to the previous example, 7.1 g. of N-(2-dimethylaminoethyl)-3-(2-fluorophenyl)-5-methoxy-indole-2-carboxamide with 3 g. of sodium hydride suspension in 70 ml. of dimethylformamide yielded 5.5 g. (82 percent) of 5-(2-dimethylaminoethyl)-10-methoxy-7H-indolo[2,3-c]quinolin-6(5H)-one, having a melting point of 285°–287°.

EXAMPLE 33

Preparation of ethyl
5-chloro-3-(2-fluorophenyl)-1-methylindole-2-carboxylate 15 g. of potassium t-butoxide was added to a solution of 32 g. of ethyl 5-chloro-3-(2-fluorophenyl)indole-2-carboxylate in 200 ml. of dimethylformamide. After stirring for 5 minutes, 12.5 ml. of dimethylsulfate was added and stirring was continued for 30 minutes. The mixture was diluted with ice/water and the precipitated solid was collected, washed with water and recrystallized from ethanol to yield 24 g. (72 percent) of ethyl 5-chloro-3-(2-fluorophenyl)-1-methylindole-2-carboxylate, having a melting point of 78°–81°.

EXAMPLE 34

Preparation of ethyl
3-(2-fluorophenyl)-2-oxopropionate
p-nitrophenylhydrazones

A solution of 29 g. of sodium nitrite in 250 ml. of water was added slowly to a suspension of 58 g. of p-nitroaniline in 170 ml. of concentrated hydrochloric acid cooled to −10°. The mixture was stirred at −10° to 0° until solution was complete. This diazonium salt solution was added to a mixture of 100 g. of ethyl 2-acetyl-3-(2-fluorophenyl)propionate, 400 ml. of ethanol, 81 g. of sodium hydroxide and 500 ml. of water cooled to −10°.

After addition of the diazonium salt solution, the reaction mixture was stirred for 1 hour at room temperature. It was extracted with 500 ml. of benzene. The product which crystallized partially from the benzene solution was collected to leave 15.6 g. of ethyl 3-(2-fluorophenyl)-2-oxopropionate p-nitrophenylhydrazone, having a melting point of 147°–149°.

Recrystallization of this material from ethanol yielded pure ethyl 3-(2-fluorophenyl)-2-oxo-propionate p-nitrophenyl hydrazone (anti-COOEt) as dark yellow crystals having a melting point of 152°–155°.

500 ml. of methylene chloride was added to the filtrate to keep all material in solution. The solution was dried and evaporated. 250 ml. of ethanol containing 7 percent of hydrogen chloride was added to the residue, and the solution was heated to boiling. After addition of water, the product crystallized on cooling to yield 52.4 g. of ethyl 3-(2-fluorophenyl)-2-oxopropionate p-nitrophenyl hydrazone (syn-COOEt), having a melting point of 118°–121°. The analytical sample was recrystallized from ethanol and had a melting point of 119°–122°.

EXAMPLE 35

Preparation of ethyl
3-(2-fluorophenyl)-5-nitroindole-2-carboxylate 350 g. of polyphosphoric acid was heated with stirring to 145°. 80 g. of a mixture of ethyl 3-(2-fluorophenyl)-2-oxopropionate p-nitrophenyl hydrazone (anti-COOEt) and ethyl 3-(2-fluorophenyl)-2-oxopropionate p-nitrophenyl hydrazone (syn-COOEt) was added in portions over a period of 15 minutes. After addition, the mixture was heated for 20 minutes at 150°–160°. After cooling to 80°, ice-water was added, and the precipitated material was collected by filtration. It was boiled up with methylene chloride. After separation of insoluble material, the filtrate was evaporated and the residue was recrystallized from $CH_2CL_2$/ethanol to yield 41.5 g. (54 percent) of ethyl 3-(2-fluorophenyl)-5-nitroindole-2-carboxylate, having a melting point of 224°–230°.

The analytical sample was purified by passing over silica gel with chloroform and by recrystallization from isopropanol and had a melting point of 232°–235°.

EXAMPLE 36

Preparation of ethyl
5-ethyl-3-(2-fluorophenyl)indole-2-carboxylate

A diazonium salt solution prepared from 24.2 g. of p-ethylaniline in 80 ml. of concentrated hydrochloric acid and 13.8 g. of sodium nitrite in 120 ml. of water was added at −10° to a mixture of 47.6 g. of ethyl 2-acetyl-3-(2-fluorophenyl)-propionate, 200 ml. of ethanol, 75 ml. of water and 38 g. of sodium hydroxide prepared at −20° to −10°. After addition, cooling was discontinued and the mixture was stirred at room temperature for 1 hour and then extracted with benzene. The benzene extracts were dried and evaporated. 400 ml. of ethanol containing 7 percent of hydrogen chloride was added to the residue. The solution was stirred and refluxed for 16 hours. The product was crystallized from the cooled reaction mixture by addition of water. It was collected, washed with water and ethanol to yield 29.3 g. (47 percent) of ethyl 5-ethyl-3-(2-fluorophenyl)indole-2-carboxylate, having a melting point of 140°–143°. Recrystallization from methylene chloride/ethanol gave pure material having a melting point of 147°–149°.

EXAMPLE 37

Preparation of ethyl
5-fluoro-3-(2-fluorophenyl)indole-2-carboxylate

In a similar manner as above, reaction of the diazonium salt prepared from 23.3 g. of p-fluoroaniline, 85 ml. of concentrated hydrochloric acid, 14.5 g. of sodium nitrite and 125 ml. of water was reacted with a mixture of 50 g. of ethyl 2-acetyl-3-(2-fluorophenyl)-propionate, 200 ml. of ethanol, 40.5 g. of sodium hydroxide and 100 ml. of water. The crude hydrazone was refluxed with 500 ml. of 1.5N ethanolic hydrogen chloride for 1 hour. The product was crystallized by addition of water, collected and washed with ethanol and hexane to yield 42 g. (66 percent) of ethyl 5-fluoro-3-(2-fluorophenyl)indole-2-carboxylate, having a melting point of 145°–147°. The analytical sample was recrystallized from methylene chloride/ethanol and had a melting point of 145°–147°.

EXAMPLE 38

Preparation of ethyl
7-chloro-5-(2-fluorophenyl)indole-2-carboxylate

The diazonium salt prepared from 25.5 g. of o-chloroaniline, 80 ml. concentrated hydrochloric acid, 13.8 g. of sodium nitrite and 120 ml. of water was reacted with 47.6 g. of ethyl 2-acetyl-3-(2-fluorophenyl)propionate, 200 ml. of ethanol, 38.5 g. of sodium hydroxide and 75 ml. of water. The formed crude hydrazone was refluxed for 16 hours in 400 ml. of 1.5N ethanolic hydrogen chloride. Crystallization by addition of water yielded 20.5 g. (32 percent) of ethyl 7-chloro-5-(2-fluorophenyl)indole-2-carboxylate, having a melting point of 130°–133°.

EXAMPLE 39

Preparation of
N-(2-dimethylaminoethyl)-5-fluoro-3-(2-fluorophenyl)indole-2-carboxamide A mixture of 20 g. of ethyl 5-fluoro-3-(2-fluorophenyl)indole-2-carboxylate and 100 ml. of 2-dimethylaminoethylamine was refluxed for 16 hours. The excess reagent was evaporated under reduced pressure, and the residue was crystallized from methylene chloride/ethanol to yield 18.3 g. (80 percent) of N-(2-dimethylaminoethyl)-5-fluoro-3-(2-fluorophenyl)indole-2-carboxamide, having a melting point of 217°14 220°.

EXAMPLE 40

Preparation of
N-(2-dimethylaminoethyl)-5-ethyl-3-(2-fluorophenyl)indole-2-carboxamide A mixture of 15 g. of ethyl 5-ethyl-3-(2-fluorophenyl)-indole-2-carboxylate and 50 ml. of 2-dimethylaminoethylamine was refluxed for 4 days. The reaction mixture was diluted with water and extracted with methylene chloride. The extracts were dried and evaporated. Crystallization of the residue from ethanol/water yielded 13.2 g. (77 percent) of N-(2-dimethylaminoethyl)-5-ethyl-3-(2-fluorophenyl)indole-2-carboxamide, having a melting point of 159°–161°. For analysis it was recrystallized from ethanol/water and had a melting point of 159°–162°.

EXAMPLE 41

Preparation of
N-(2-dimethylaminoethyl)-3-(2-fluorophenyl)-5-nitroindole-2-carboxamide A mixture of 20 g. of ethyl 3-(2-fluorophenyl)-5-nitroindole-2-carboxylate and 50 ml. of 2-dimethylaminoethylamine was refluxed for 16 hours. The reaction mixture was concentrated to dryness and the residue was recrystallized from methylene chloride/ethanol to yield 17.3 g. (76 percent) of N-(2-dimethylaminoethyl)-3-(2-fluorophenyl)-5-nitroindole-2-carboxamide, having a melting point of 203°–205°.

EXAMPLE 42

Preparation of
7-chloro-N-(2-dimethylaminoethyl)-3-(2-fluorophenyl)indole-2-carboxamide 15.5 g. of ethyl 7-chloro-3-(2-fluorophenyl)indole-2-carboxylate and 75 ml. of 2-dimethylaminoethylamine was refluxed for 48 hours. The reaction mixture was diluted with water and extracted with methylene chloride. The extracts were dried and evaporated. Crystallization of the residue from methylene chloride/cyclohexane yielded 11.3 g. (65 percent) of 7-chloro-N-(2-dimethylaminoethyl)-3-(2-fluorophenyl)indole-2-carboxamide, having a melting point of 119°–121°. The analytical sample was recrystallized from methylene chloride/hexane and had a melting point of 119°14 122°.

EXAMPLE 43

Preparation of
5-chloro-3-(2-fluorophenyl)-N-(2-methylaminoethyl)-indole-2-carboxamide A mixture of 10 g. of ethyl 5-chloro-3-(2-fluorophenyl)-indole-2-carboxylate and 15 ml. of 2-methylaminoethylamine was refluxed for 18 hours. The excess reagent was evaporated and the residue was crystallized from ethanol/water to yield 10.4 g. of product having a melting point of 158°–163°. Recrystallization from ethanol/water afforded 6.5 g. (60 percent) of 5-chloro-3-(2-fluorophenyl)-N-(2-methylaminoethyl)indole-2-carboxamide, having a melting point of 173°–177°. The analytical sample was recrystallized again and had a melting point of 178°–180°.

EXAMPLE 44

Preparation of
N-(2-aminoethyl)-5-chloro-3-(2-fluorophenyl)-indole-2-carboxamide 10 g. of ethyl 5-chloro-3-(2-fluorophenyl)indole-2-carboxylate and 50 ml. of ethylene diamine was heated to reflux for 16 hours. The reaction mixture was concentrated to dryness and the residue was crystallized from chloroform/hexane to yield 9 g. (86 percent) of N-(2-aminoethyl)-5-chloro-3-(2-fluorophenyl)-indole-2-carboxamide, having a melting point of 210°–213°. For analysis it was recrystallized from methanol/water and had a melting point of 214°–216°.

EXAMPLE 45

Preparation of
5-chloro-3-(2-fluorophenyl)-N-(2-morpholinoethyl)indole-2-carboxamide A mixture of 3.17 g. of ethyl 5-chloro-3-(2-fluorophenyl)-indole-2-carboxylate and 10 ml. of N-(2-aminoethyl)morpholine was stirred and refluxed for 4 hours. After dilution with water, the product was extracted with methylene chloride. The extracts were dried and evaporated, and the residue was recrystallized from ether to yield 2.7 g. (67 percent) of 5-chloro-3-(2-fluorophenyl)-N-(2-morpholinoethyl)indole-2-carboxamide, having a melting point of 193°–197°. The analytical sample was recrystallized from methylene chloride/ethanol and had a melting point of 200°–202°.

EXAMPLE 46

Preparation of
5-chloro-N-(3-dimethylaminopropyl)-3-(2-fluorophenyl)-indole-2-carboxamide A mixture of 15 g. of ethyl 5-chloro-3-(2-fluorophenyl)-indole-2-carboxylate and 75 ml. of 3-dimethylaminopropylamine was stirred and refluxed for 16 hours. The excess amine was evaporated and the residue was crystallized from methylene chloride/hexane to yield 16.4 g. (92 percent) of 5-chloro-N-(3-dimethylaminopropyl)-3-(2-fluorophenyl)indole-2-carboxamide, having a melting point of 154°–156°. For analysis is was recrystallized from methylene chloride/hexane and had a melting point of 155°–157°.

EXAMPLE 47

Preparation of
N-(3-aminopropyl)-5-chloro-3-(2-fluorophenyl)-indole-2-carboxamide 15 g. of ethyl 5-chloro-3-(2-fluorophenyl)indole-2-carboxylate was heated in 50 ml. of 1,3-diaminopropane with reflux for 2 hours. The reaction mixture was diluted with water and extracted with methylene chloride. The extracts were dried and evaporated. Crystallization of the residue from methylene chloride/hexane yielded 13.2 g. (81 percent) of N-(3-aminopropyl)-5-chloro-3-(2-fluorophenyl)indole-2-carboxamide, having a melting point of 172°–175°. The analytical sample was recrystallized from the same solvents and had a melting point of 173°–175°.

EXAMPLE 48

Preparation of 5-chloro-3-(2-fluorophenyl)-N-(3-morpholinopropyl)indole-2-carboxamide A mixture of 15 g. of ethyl 5-chloro-3-(2-fluorophenyl)-indole-2-carboxylate and 25 ml. of N-(3-aminopropyl)morpholine was refluxed for 4 hours. After dilution with water, the product was extracted with methylene chloride. The extracts were dried and evaporated. Crystallization of the residue from ether yielded 15.3 g. (76 percent) of 5-chloro-3-(2-fluorophenyl)-N-(3-morpholinopropyl)indole-2-carboxamide, having a melting point of 112°–115°.

EXAMPLE 49

Preparation of 10-chloro-5-(2-methylaminoethyl)-7H-indolo[2,3-c]-quinolin-6(5H)-one 9.12 g. of sodium hydride suspension (50 percent in mineral oil) was added to 21.8 g. of 5-chloro-3-(2-fluorophenyl)-N-(2-methylaminoethyl)indole-2-carboxamide dissolved in 250 ml. of dry diglyme and 150 ml. of dimethylsulfoxide. The mixture was gradually heated to reflux for 10 minutes with stirring under nitrogen. After cooling, it was diluted with water. The precipitated solids were collected, washed with water and methanol and recrystallized from methylene chloride/methanol to yield 14.9 g. (72 percent) of 10-chloro-5-(2-methylaminoethyl)-7H-indolo[2,3-c]quinolin-6(5H)-one, having a melting point of 263°–265°. For analysis it was recrystallized from the same solvents and had a melting point of 264°–266°.

EXAMPLE 50

Preparation of 5-(2-aminoethyl)-10-chloro-7H-indolo[2,3,-c]-quinolin-6(5H)-one 9.12 g. of sodium hydride suspension (50 percent in mineral oil) was washed with hexane and added to a solution of 21 g. of N-(2-aminoethyl)-5-chloro-3-(2-fluorophenyl)indole-2-carboxamide in 100 ml. of diglyme and 100 ml. of dimethylsulfoxide. The reaction mixture was heated to reflux (about 160°) for 10 minutes with stirring under nitrogen. After cooling, water was added and the precipitated crystals were collected, washed with water and methanol and recrystallized from methylene chloride/methanol to yield 13.7 g. (70 percent) of 5-(2-aminoethyl)-10-chloro-7H-indolo[2,3-c]quinolin-6(5H)-one, having a melting point of 262°–265°.

EXAMPLE 51

Preparation of 10-chloro-5-(2-morpholinoethyl)-7H-indolo[2,3-c]-quinolin-6(5H)-one 4.1 g. of sodium hydride suspension (50 percent in mineral oil) was washed with hexane and added to a solution of 11.5 g. of 5-chloro-3-(2-fluorophenyl)-N-(2-morpholinoethyl)indole-2-carboxamide in 200 ml. of dimethylformamide. The mixture was heated to reflux for 10 minutes with stirring under nitrogen. Water was added for cooling and the crystalline precipitate was collected, washed with water, methanol and ether. Recrystallization from boiling dimethylformamide yielded 8.9 g. (82 percent) of 10-chloro-5-(2-morpholinoethyl)-7H-indolo-[2,3-c]quinolin-6(5H)-one, having a melting point of 334°–336°.

EXAMPLE 52

Preparation of 10-chloro-5-(3-dimethylaminopropyl)-7H-indolo-[2,3-c]quinolin-6(5H)-one Under the same conditions as described above, reaction of 17.7 g. of 5-chloro-N-(3-dimethylaminopropyl)-3-(2-fluorophenyl)-indole-2-carboxamide with 6.8 g. sodium hydride suspension in 250 ml. of dimethylformamide yielded after recrystallization from boiling dimethylformamide 13.5 g. (81 percent) of 10-chloro-5-(3-dimethylaminopropyl)-7H-indolo[2,3-c]quinolin-6(5H)-one, having a melting point of 286°–288°.

EXAMPLE 53

Preparation of 5-(3-aminopropyl)-10-chloro-7H-indolo[2,3-c]-quinolin-6(5H)-one 5.5 g. of sodium hydride suspension was added to a solution of 13.2 g. of N-(3-aminopropyl)-5-chloro-3-(2-fluorophenyl)-indole-2-carboxamide in 175 ml. of diglyme and 75 ml. of dimethylsulfoxide. The mixture was heated to reflux (about 160°) for 10 minutes with stirring under nitrogen. The product, precipitated by addition of water, was collected and recrystallized from ethanol/water to yield 3.7 g. (30 percent) of 5-(3-aminopropyl)-10-chloro-7H-indolo[2,3-c]quinolin-6(5H)-one, having a melting point of 264°–267°.

EXAMPLE 54

Preparation of 10-chloro-5-(3-morpholinopropyl)-7H-indolo[2,3-c]-quinolin-6(5H)-one A mixture of 15.3 g. of 5-chloro-3-(2-fluorophenyl)-N-(3-morpholinopropyl)indole-2-carboxamide, 5.2 g. of sodium hydride suspension and 200 ml. of dimethylformamide was heated to reflux for 10 minutes with stirring under nitrogen. Dilution with water and recrystallization of the precipitated material from dimethylformamide yielded 10.8 g. (76 percent) of 10-chloro-5-(3-morpholinopropyl)-7H-indolo[2,3-c]quinolin-6(5H)-one, having a melting point of 265°–269°. For analysis it was recrystallized from tetrahydrofurane and had a melting point of 268°–270°.

EXAMPLE 55

Preparation of 5-(2-dimethylaminoethyl)-10-ethyl-7H-indolo-[2,3-c]quinolin-6(5H)-one Reaction of 13.2 g. of N-(2-dimethylaminoethyl)-5-ethyl-3-(2-fluorophenyl)indole-2-carboxamide with 5.4 g. of sodium hydride suspension in 200 ml. of dimethylformamide yielded, as described above, 10.1 g. (81 percent) of 5-(2-dimethylaminoethyl)-10-ethyl-7H-indolo[2,3-c]quinolin-6(5H)-one, having a melting point of 266°–268° after recrystallization from methylene chloride/ethanol.

EXAMPLE 56

Preparation of
5-(2-dimethylaminoethyl)-10-fluoro-7H-indolo[2,3-c]quinolin-6-(5H)-one 18.3 g. of N-(2-dimethylaminoethyl)-5-fluoro-3-(2-fluorophenyl)-indole-2-carboxamide and 7.7 g. of sodium hydride suspension were reacted, as described above, in 200 ml. of dimethylformamide. Recrystallization of the product from methylene chloride/methanol yielded 16.5 g. (96 percent) of 5-(2-dimethylaminoethyl)-10-fluoro-7H-indolo[2,3-c]quinolin-6(5H)one, having a melting point of 285°–288°.

EXAMPLE 57

Preparation of
5-(2-dimethylaminoethyl)-10-nitro-7H-indolo-[2,3-c]quinolin-6(5H)-one Reaction of 1 g. of N-(2-dimethylaminoethyl)-5-nitro-3-(2-fluorophenyl)indole-2-carboxamide with 0.4 g. of sodium hydride suspension in 20 ml. of diglyme and 10 ml. of dimethylsulfoxide yielded 0.7 g. (74 percent) of 5-(2-dimethylaminoethyl)-10-nitro-7H-indolo[2,3-c]quinolin-6(5H)-one, having a melting point of 316°–320°. It was recrystallized from dimethylformamide and had a melting point of 320°–323°.

EXAMPLE 58

Preparation of
8-chloro-5-(2-dimethylaminoethyl)-7H-indolo-[2,3-c]quinolin-6(5H)-one 11.3 g. of 7-chloro-N-(2-dimethylaminoethyl)-3-(2-fluorophenyl)-indole-2-carboxamide was reacted with 4.5 g. of sodium hydride suspension in 200 ml. of dimethylformamide. The product obtained upon dilution of the reaction mixture with water was collected and recrystallized from methylene chloride/ethanol to yield 9.5 g. (89 percent) of 8-chloro-5-(2-dimethylaminoethyl)-7H-indolo[2,3-c]quinolin-6(5H)-one, having a melting point of 219°–221°.

EXAMPLE 59

Preparation of
10-chloro-7H-indolo[2,3-c]quinolin-6(5H)-one 29 g. of 5-chloro-3-(2-fluorophenyl)indole-2-carboxamide was reacted with 14.4 g. of sodium hydride suspension in 800 ml. of dimethylformamide, as described above. The product was crystallized from the reaction mixture by addition of water. It was collected, washed with water, methanol and ether to yield 26.6 g. (98 percent) of 10-chloro-7H-indolo[2,3-c]quinolin-6(5H)-one, having a melting point of 334°–336°. The analytical sample was recrystallized repeatedly from methylene chloride/methanol and had a melting point of 348°–350°.

EXAMPLE 60

Preparation of
10-chloro-7-(2-dimethylaminoethyl)-7H-indolo-[2,3-c]quinolin-6(5H)-one 14.4 g. of sodium hydride suspension was added to a solution of 26.6 g. of the above crude 10-chloro-7H-indolo[2,3-c]quinolin-6(5H)-one in 500 ml. of dimethylformamide. The mixture was heated on the steambath for 15 minutes. After cooling, 17.3 g. of 2-dimethylaminoethyl chloride hydrochloride was added. After the hydrogen evolution had subsided, the mixture was heated on the steambath for 30 minutes and then was diluted with water and extracted with methylene chloride. The extracts were washed with water, dried and evaporated. Crystallization from ether yielded 12.3 g. (36.6 percent) of 10-chloro-7-(2-dimethylaminoethyl)-7H-indolo[2,3-c]quinolin-6(5H)-one, having a melting point of 280°–286°. For analysis it was recrystallized from dimethylformamide and had a melting point of 286°–289°.

EXAMPLE 61

Preparation of
10-chloro-5-(2-dimethylaminoethyl)-7-methyl-7H-indolo[2,3-c]quinolin-6(5H)-one a. 17 G. of 10-chloro-5-(2-dimethylaminoethyl)-7H-indolo-[2,3-c]quinolin-6(5H)-one were dissolved in 2 l. of dimethylformamide by warming to 80°. A 50 percent suspension of sodium hydride in mineral oil (8 g.) was added. When the temperature reached 50°, 4 ml. of methyliodide was added and stirring was continued for 15 minutes. The reaction mixture was diluted with water and extracted with benzene. The benzene extracts were washed with water, dried over sodium sulfate and evaporated. The residue was taken up with benzene, and the insoluble material was separated. The filtrate was concentrated and crystallized by addition of hexane to yield 12.4 g. or 70 percent of 10-chloro-5-(2-dimethylaminoethyl)-7-methyl-7H-indolo[2,3-c]quinolin-6(5H)-one, which after recrystallization from benzene/hexane had a melting point of 150°–152°.

b. A mixture of 37.4 g. of 5-chloro-N-(2-dimethylaminoethyl)-3-(2-fluorophenyl)-1-methylindole-2-carboxamide, 7.5 g. of sodium hydride suspension (50 percent in mineral oil) and 200 ml. of dimethylformamide was heated to reflux for 10 minutes. The product was precipitated by the addition of water, collected, washed with water and dissolved in methylene chloride. Crystallization of the residue from benzene/hexane gave 31.7 g. (89 percent) of 10-chloro-5-(2-dimethylaminoethyl)-7-methyl-7H-indolo[2,3-c]quinolin-6(5H)-one, having a melting point of 150°–152°.

EXAMPLE 62

Preparation of
10-chloro-5-(2-dimethylamino)-7-ethyl-7H-indolo-[2,3-c]quinolin-6(5H)-one 10.2 g. of 10-chloro-5-(2-dimethylaminoethyl)-7H-indolo[2,3-c]-quinolin-6(5H)-one were dissolved by heating in 1 l. of dimethylformamide. After cooling to 90°, 4.5 g. of sodium hydride suspension (50 percent in mineral oil) was added and stirring was continued for 5 minutes. When the temperature reached 60°, 6.6 g. of ethyliodide was added. After 15 minutes the reaction mixture was worked up as described in the previous example to yield 7.4 g. (67 percent) of 10-chloro-5-(2-dimethylaminoethyl)-7-ethyl-7H-indolo[2,3-c]quinolin-6(5H)-one with a melting point of 115°–120°, crystallized from benzene/hexane. For analysis, it was recrystallized from benzene/hexane and had a melting point of 127°. A different more stable crystalline modification with a melting point of 142°–143° was obtained in a second experiment.

EXAMPLE 63

Preparation of
7-allyl-10-chloro-5-(2-dimethylaminoethyl)-7H-indolo[2,3-c]quinolin-6(5H)-one Alkylation of 10.2 g. of 10-chloro-5-(2-dimethylaminoethyl)-7H-indolo[2,3-c]quinolin-6(5H)-one in 1 l. of dimethylformamide with 4.5 g. of sodium hydride suspension and 4 ml. of allylbromide gave under the same conditions 7.6 g. (66 percent) of 7-allyl-10-chloro-5-(2-dimethylaminoethyl)-7H-indolo[2,3-c]-quinolin-6(5H)-one, having a melting point of 143°–145°.

EXAMPLE 64

Preparation of
10-chloro-5-(2-dimethylaminoethyl)-7-methoxy-methyl-7H-indolo[2,3-c]quinolin-6(5H)-one Alkylation of 10.2 g. of 10-chloro-5-(2-dimethylaminoethyl)-7H-indolo[2,3-c]quinolin-6(5H)-one in 1 l. of dimethylformamide with 4.5 g. of sodium hydride suspension and 3.6 ml. of chlorodimethylether yielded under the same conditions 8 g. (70 percent) of 10-chloro-5-(2-dimethylaminoethyl)-7-methoxymethyl-7H-indolo[2,3-c]quinolin-6(5H)-one with a melting point of 127°–129°.

EXAMPLE 65

Preparation of
5-chloro-3-(2-fluorophenyl)-N-methyl-indole-2-carboxamide

A mixture of 57.9 g. of 5-chloro-3-(2-fluorophenyl)indole-2-carboxylic acid, 50 g. of phosphorus pentachloride and 1 l. of methylene chloride was stirred at room temperature for 20 minutes. An aqueous solution of methylamine was then added with ice cooling until the reaction mixture was alkaline. The precipitate formed by the addition of hexane was collected. Recrystallization from methylene chloride/ethanol yielded 42.3 g. (70 percent) of 5-chloro-3-(2-fluorophenyl)-N-methyl-indole-2-carboxamide with a melting point of 218°–221°.

EXAMPLE 66

Preparation of
10-chloro-5-methyl-7H-indolo[2,3-c]quinolin-6(5H)-one

A mixture of 6.05 g. of 5-chloro-3-(2-fluorophenyl)-N-methylindole-2-carboxamide, 2.9 g. of sodium hydride suspension (50 percent in mineral oil) and 30 ml. of dimethylformamide was heated to reflux for 10 minutes under an atmosphere of nitrogen. The reaction mixture was poured into water. The precipitate was collected, washed with water and methanol and was recrystallized from dimethylformamide to yield 4 g. (71 percent) of 10-chloro-5-methyl-7H-indolo[2,3-c]quinolin-6(5H)-one having a melting point of >360°.

EXAMPLE 67

Preparation of
5-chloro-3-(2-fluorophenyl)-N-(2-hydroxyethyl)-indole-2-carboxamide A mixture of 20 g. of methyl-5-chloro-3-(2-fluorophenyl)-indole-2-carboxylate, (mp 178°–180°, prepared analogously to the known ethyl ester) and 100 ml. of ethanolamine was refluxed for 10 minutes. The reaction mixture was then partitioned between water and ether. The precipitate was collected and recrystallized from benzene to give 13.6 g. (62 percent) of 5-chloro-3-(2-fluorophenyl)-N-(2-hydroxyethyl)indole-2-carboxamide having a melting point of 179°–181°. For analysis, it was recrystallized from methylene chloride and had a melting point of 181°–183°.

EXAMPLE 68

Preparation of
10-chloro-5-(2-hydroxyethyl)-7H-indolo[2,3-c]-quinolin-6(5H)-one

A mixture of 6.65 g. of 5-chloro-3-(2-fluorophenyl)-N-(2-hydroxyethyl)indole-2-carboxamide, 2.9 g. of sodium hydride suspension (50 percent in mineral oil) and 100 ml. of dimethylformamide was heated to reflux for 12 minutes under nitrogen. The precipitate formed by the addition of water was collected, washed with water and dried to give 3.1 g. (50 percent) of 10-chloro-5-(2-hydroxyethyl)-7H-indolo[2,3-c]quinolin-6(5H)-one, having a melting point of 314°–319°. The analytical sample was recrystallized from dimethylformamide/ether, and had a melting point of 318°–320°.

EXAMPLE 69

Preparation of
5-chloro-N-(2-dimethylaminoethyl)-3-(2-fluorophenyl)-1-methylindole-2-carboxamide A mixture of 30.3 g. of 5-chloro-3-(2-fluorophenyl)-1-methylindole-2-carboxylic acid (mp 232°–234°, obtained by hydrolysis of corresponding ester), 100 ml. of methylene chloride and 25 ml. of thionylchloride was refluxed for 6 hours. After evaporation, the residue was dissolved in methylene chloride and added to a solution of 20 ml. of 2-dimethylaminoethylamine in 100 ml. of methylene chloride. 100 Ml. of 10 percent aqueous sodium carbonate was then added and the two-phase system was stirred for 30 minutes at room temperature. The organic layer was separated, dried and evaporated. Crystallization of the residue from ether/methylene chloride/hexane yielded 29 g. (77.5 percent) of 5-chloro-N-(2-dimethylaminoethyl)-3-(2-fluorophenyl)-1-methylindole-2-carboxamide, having a melting point of 95°–100°. For analysis, it was recrystallized from ether/hexane and had a melting point of 100°–101°.

EXAMPLE 70

Preparation of
7-cyanomethyl-10-chloro-5-methyl-7H-indolo[2,3-c]-quinolin-6(5H)-one 1.4 G. of sodium hydride suspension was added to a suspension of 2.82 g. of 10-chloro-5-methyl-7H-indolo[2,3-c]quinolin-6(5H)-one in 100 ml. of dimethylformamide. The mixture was heated to 100° to form a solution and cooled again to 10°, whereupon 3.25 g. of chloroacetonitrile was added. After stirring for 20 minutes at room temperature, a precipitate was formed by the addition of water. Recrystallization of the precipitate from dimethylformamide yielded 2.3 g. (75 percent) of 7-cyanomethyl-10-chloro-5-methyl-7H-indolo[2,3-c]quinolin-6(5H)-one, having a melting point of 305°–308°.

EXAMPLE 71

Preparation of
7-cyanomethyl-10-chloro-5-ethyl-7H-indolo[2,3-c]-quinolin-6(5H)-one Similarly, the alkylation of 5.95 g. of 10-chloro-5-ethyl-7H-indolo[2,3-c]quinolin-6-(5H)-one with 2.9 g. of sodium hydride suspension (50 percent in mineral oil) and 6.5 g. of chloroacetonitrile in 100 ml. of dimethylformamide yielded 6.1 g. (91 percent) of 7-cyanomethyl-10-chloro-5-ethyl-7H-indolo[2,3-c]-quinolin-6(5H)-one, having a melting point of 263°–267°. For analysis, it was recrystallized from dimethylformamide and had a melting point of 265°–267°.

EXAMPLE 72

Preparation of
7-(2-aminoethyl)-10-chloro-5-ethyl-7H-indolo-[2,3-c]quinolin-6(5H)-one 5 g. of 7-cyanomethyl-10-chloro-5-ethyl-7H-indolo[2,3-c]-quinolin-6(5H)-one was dissolved in 200 ml. of boiling dimethylformamide. After cooling, 200 ml. of tetrahydrofuran, 100 ml. of ethanol and Raney nickel were added. The mixture was hydrogenated for 2½ hours at atmospheric pressure. The catalyst was separated by filtration and the filtrate was evaporated. Crystallization of the residue from ethanol yielded 2.9 g. (57 percent) of 7-(2-aminoethyl)-10-chloro-5-ethyl-7H-indolo[2,3-c]quinolin-6(5H)-one, which after recrystallization from ethanol had a melting point of 166°–169°.

EXAMPLE 73

Preparation of
7-(2-aminoethyl)-10-chloro-5-methyl-7H-indolo-[2,3-c]quinolin-6(5H)-one Hydrogenation of 5 g. of 7-cyanomethyl-10-chloro-5-methyl-7H-indolo[2,3-c]quinolin-6(5H)-one with Raney nickel in a mixture of 250 ml. of dimethylformamide, 250 ml. of tetrahydrofuran and 250 ml. of ethanol yielded 2.7 g. (53 percent) of 7-(2-amino-ethyl)-10-chloro-5-methyl-7H-indolo[2,3-c]quinolin-6(5H)-one, having a melting point of 222°–224° after recrystallization from methylene chloride/ethanol.

EXAMPLE 74

Preparation of
10-chloro-5-(2-dimethylaminoethyl)-7H-indolo[2,3-c]quinolin-6(5H)-one N/107 /oxide 2 G. of 10-chloro-5-(2-dimethylaminoethyl)-7H-indolo[2,3-c]-quinolin-6(5H)-one were suspended in 1 l. of methylene chloride and 70 ml. of ethanol. The mixture was heated to reflux and removed from the steam bath, when 1.15 g. of m-chloroperbenzoic acid was added. After standing for 15 minutes, the solution was filtered, and the filtrate was evaporated. The residue was treated with ethanolic hydrogen chloride and 200 ml. of ether. After boiling on a steam bath for a few minutes the solids were collected and washed with ether. The product was partitioned between 500 ml. of methylene chloride containing 10 percent of ethanol and 10 percent aqueous sodium carbonate. The organic phase was separated, dried over sodium sulfate and evaporated. The crystalline residue was slurried with ethylacetate and collected to give 1.5 g. (71 percent) of 10-chloro-5-(2-dimethylaminoethyl)-7H-indolo[2,3-c]quinolin-6(5H)-one N/ω/oxide as colorless crystals. For analysis, it was recrystallized from methylene chloride/methanol/ethylacetate and had a melting point of 280°–290° dec.

EXAMPLE 75

Preparation of
10-chloro-5-(2-dimethylaminoethyl)-7-methyl-7H-indolo[2,3-c]quinolin-6(5H)-one N/ω/oxide 2 g. of m-chloroperbenzoic acid was added to a solution of 3.5 g. of 10-chloro-5-(2-dimethylaminoethyl)-7-methyl-7H-indolo-[2,3-c]quinolin-6(5H)-one in 100 ml. of methylene chloride. After standing at room temperature for 1 hour, the mixture was diluted with 100 ml. of ether. The solids were collected and suspended in 100 ml. of methanol. To the warm suspension was added 20 ml. of 10 percent aqueous sodium carbonate. After partial evaporation under reduced pressure, the mixture was diluted with water. The crystalline material which formed was collected and recrystallized from acetone/methanol to yield 2.8 g. (76 percent) of 10-chloro-5-(2-dimethylaminoethyl)-7-methyl-7H-indolo[2,3-c]quinolin-6(5H)-one N/ω/oxide, having a melting point of 220°–222° dec.

EXAMPLE 76

Preparation of
10-chloro-5-(2-dimethylaminoethyl)-7-ethyl-7H-indolo[2,3-c]quinolin-6(5H)-one N/ω/oxide 4.3 G. of m-chloroperbenzoic acid were added to a solution of 7.4 g. of 10-chloro-5-(2-dimethylaminoethyl)-7-ethyl-7H-indolo[2,3-c]quinolin-6(5H)-one in 100 ml. of methylene chloride. After standing at room temperature for 30 minutes, the mixture was partitioned between methylene chloride containing 10 percent ethanol and 10 percent aqueous sodium carbonate. The organic phase was separated, washed with sodium carbonate solution and water, dried over sodium sulfate and evaporated. Crystallization of the residue from ethanol/ethylacetate yielded 5.5 g. (72 percent) of 10-chloro-5-(2-dimethylaminoethyl)-7-ethyl-7H-indolo[2,3-c]quinolin-6(5H)-one, having a melting point of 202°–104° dec. For analysis, it was recrystallized from acetone/methanol.

EXAMPLE 77

Preparation of 3-azido-1-methyl-4-phenylcarbostyril

To a stirred suspension of 10.0 g of 3-azido-4-phenylcarbostyril in 125 ml. of dry dimethylformamide was added 2.2 g. of a 57 percent dispersion of sodium hydride in oil. After stirring at room temperature for about 45 minutes, the mixture was filtered to remove a small amount of insoluble material. To the clear solution was added 5 ml. of methyl iodide. The solution soon turned from an orange color to light yellow, accompanied by the formation of a precipitate. After 1 hour, the mixture was diluted with water and 10 g. (95 percent) of 3-azido-1-methyl-4-phenylcarbostyril, mp indefinite in the range of 140°–150° with decomposition, was collected. This material was pure by tlc. After recrystallizations from dimethylformamide-methanol, yellow needles were obtained, having a melting point of 140°–150° dec.

EXAMPLE 78

Preparation of
5-methyl-7H-indolo[2,3-c]quinolin-6(5H)-one

A suspension of 67.6 g. of 3-azido-1-methyl-4-phenylcarbostyril in 1150 ml. of toluene was heated under reflux for 5 hours. After cooling, the solids obtained were collected, washed with toluene followed by petroleum ether, to give 52.1 g. (87 percent) of 5-methyl-7H-indolo[2,3-c]quinolin-6(5H)-one. An analytical sample was prepared by recrystallization from dimethylformamide to give pale yellow needles of 5-methyl-7H-indolo[2,3-c]quinolin-6(5H)-one, having a melting point of 293°–296°.

EXAMPLE 79

Preparation of
7-(2-diethylaminoethyl)-5-methyl-7H-indolo[2,3-c]-quinolin-6(5H)-one To a stirred suspension of 37.0 g. of 5-methyl-7H-indolo-[2,3-c]quinolin-6(5H)-one in 375 ml. of dry dimethylformamide was added at room temperature 223 mmoles of sodium hydride (50 percent dispersion in oil) in portions and the mixture was stirred at room temperature for 45 minutes until the starting material dissolved. Then 92.5 ml. of a 3.2 M solution in toluene of diethylaminoethyl chloride was added, and the mixture was stirred at room temperature for 45 minutes. On evaporation to dryness, the residue was partitioned between methylene chloride and water. The methylene chloride layer was separated, washed with water, dried and evaporated. The residue was crystallized from hexane to give 43.2 g. (84 percent) of 7-(2-diethylaminoethyl)-5-methyl-7H-indolo[2,3-c]quinolin-6(5H)-one as light yellow needles having a melting point of 102°–104°.

EXAMPLE 80

Preparation of
6-(2-diethylaminoethylamino)-7H-indolo[2,3-c]-quinoline dihydrobromide The title compound was synthesized according to the procedure described in W. O. Kermack et al., J. Chem. Soc., 317 (1940). The 6-(2-diethylaminoethylamino)-7H-indolo[2,3-c]quinoline dihydrobromide was obtained in 73 percent yield and had a melting point of 270°–272° (lit mp 270°).

EXAMPLE 81

Preparation of
6.10-dichloro-7H-indolo[2,3-c]quinoline

This compound was synthesized according to the procedure described in W. O. Kermack et al., supra. The 6,10-dichloro-7H-indolo[2,3-c]quinoline was obtained in 40 percent yield and had a melting point of 257°–259° (lit mp 250°).

EXAMPLE 82

Preparation of
10-chloro-6-(2-diethylaminoethylamino)-7H-indolo[2,3-c]quinoline

A mixture of 5.00 g. of 6,10-dichloro-7H-indolo[2,3-c]-quinoline and 5.0 ml. of N,N-diethylaminoethylamine was heated at 150° for 6 hours under an atmosphere of nitrogen. On cooling, the glassy brown viscous oil was dissolved in a minimum of ethanol of boiling. The ethanol insolubles were removed by filtration, and the ethanolic solution was treated with ethanolic hydrogen bromide. The light yellow dihydrobromide which formed, was collected by filtration, washed with acetone, suspended in water, and treated with 3 N sodium hydroxide. The free base was extracted into ether. The ethereal layer was dried over anhydrous sodium sulfate, and evaporated to dryness in vacuo. The residue on crystallization from acetonitrile yielded 3.60 g. (57 percent) of 10-chloro-6-(2-diethylaminoethylamino)-7H-indolo[2,3-c]quinoline as yellow prisms, mp 217°–219°. An analytical sample was prepared by recrystallization from acetonitrile to yield 10-chloro-6-(2-diethylaminoethylamino)-7H-indolo[2,3-c]quinoline as yellow prisms, having a melting point of 219°–220°.

EXAMPLE 83

Preparation of
6,10-dichloro-7-(2-diethylaminoethyl)-7H-indolo-[2,3-c]quinoline

A mixture of 2.87 g. of 6,10-dichloro-7H-indolo[2,3-c]-quinoline, 720 mg. of sodium hydride as a 50 percent dispersion in oil, and 25 ml. of dimethylformamide was stirred at room temperature for 0.50 hours. To this mixture was added 5.0 ml. of a solution of diethylaminoethyl chloride (a 3.20 M solution in toluene) and the mixture was stirred at room temperature for 1-½ hours. The excess hydride was decomposed with water, and the resulting mixture was evaporated in vacuo. The residue was partitioned between ether and water. The ethereal layer was dried over anhydrous sodium sulfate, and evaporated to dryness in vacuo. The residue on crystallization from hexane yielded 2.00 g. (52 percent) of 6,10-dichloro-7-(2-diethylaminoethyl)-7H-indolo[2,3-c]quinoline as yellow prisms having a melting point of 83°–85°. An analytical sample was prepared by recrystallization from hexane and yielded light yellow prisms of 6,10-dichloro-7-(2-diethylaminoethyl)-7H-indolo[2,3-c]-quinoline, having a melting point of 83°–85°.

EXAMPLE 84

Capsule Formulation

| Capsule Formulation | |
|---|---|
|  | Per Capsule |
| 10-Chloro-5-(2-dimethylaminoethyl)-7H-indolo[2,3-c]quinolin-6(5H)-one | 250 mg. |
| Lactose | 60 mg. |
| Corn Starch | 35 mg. |
| Magnesium Stearate | 5 mg. |
| Total Weight | 350 mg. |

Procedure:

1. All of the ingredients are mixed until thoroughly blended in a suitable size container.
2. The powder is filled into No. 2, two-piece, hard shell gelatin capsules to an approximate fill weight of 350 mg. using a Parke Davis capsulating machine.

EXAMPLE 85

Tablet Formulation

| Tablet Formulation | Per Tablet |
|---|---|
| 10-Chloro-5-(2-dimethylaminoethyl)-7H-indolo[2,3-c]quinolin-6(5H)-one | 200 mg. |
| Dicalcium Phosphate Dihydrate, Unmilled | 235 mg. |
| Corn Starch | 70 mg. |
| FD and C Yellow No. 5 - Aluminum Lake 25 percent | 2 mg. |
| Durkee 117 | 25 mg. |
| Calcium Stearate | 3 mg. |
| Total Weight | 535 mg. |

Procedure
1. All the ingredients are mixed thoroughly and Fitzed (Model D) using a No. 1A screen, medium speed.
2. The mixture is remixed and slugged.
3. The slugs are screened on an Oscillator through a No. 14 mesh screen and compressed on an "E" machine.

EXAMPLE 86

Capsule Formulation

| Capsule Formulation | Per Capsule |
|---|---|
| 10-Chloro-5-(2-dimethylaminoethyl)-7H-indolo[2,3-c]quinolin-6(5H)-one | 50 mg. |
| Lactose, USP | 125 mg. |
| Corn Starch, USP | 30 mg. |
| Talc, USP | 5 mg. |
| Total Weight | 210 mg. |

Procedure:
1. The 10-chloro-5-(2-dimethylaminoethyl)-7H-indolo[2,3-c]-quinolin-6(5H)-one is mixed with lactose and corn starch in a suitable mixer.
2. The mixture is further blended by passing through a Fitzpatrick Comminuting Machine with a No. 1A screen with knives forward.
3. The blended power is returned to the mixer, the talc is added and blended thoroughly.
4. The mixture is filled into No. 4 hard shell gelatin capsules on a Parke Davis capsulating machine.

EXAMPLE 87

Tablet Formulation

| Tablet Formulation | Per Tablet |
|---|---|
| 10-Chloro-5-(2-dimethylaminoethyl)-7H-indolo[2,3-c]quinolin-6(5H)-one | 25 mg. |
| Dicalcium Phosphate Dihydrate, Unmilled | 175 mg. |
| Corn Starch | 24 mg. |
| Magnesium Stearate | 1 mg. |
| Total Weight | 225 mg. |

Procedure:
1. The 10-chloro-5-(2-dimethylaminoethyl)-7H-indolo[2,3-c]-quinolin-6(5H)-one and corn starch are mixed together and passed through a No. 00 screen in Model "J" Fitzmill with hammers forward.
2. This permix is then mixed with dicalcium phosphate and one-half of the magnesium stearate, passed through a No. 1A screen in Model "J" Fitzmill with knives forward, and slugged.
3. The slugs were passed through a No. 2A plate in a Model "D" Fitzmill at slow speed with knives forward, and the remaining magnesium stearate is added.
4. The mixture is then mixed and compressed.

EXAMPLE 88

Tablet Formulation

| Tablet Formulation | Per Tablet |
|---|---|
| 10-Chloro-5-(2-dimethylaminoethyl)-7H-indolo[2,3-c]quinolin-6(5H)-one | 100 mg. |
| Lactose, USP | 202 mg. |
| Corn Starch, USP | 80 mg. |
| Prehydrolyzed Corn Starch | 20 mg. |
| Calcium Stearate | 8 mg. |
| Total Weight | 410 mg. |

Procedure:
1. The 10-chloro-5-(2-dimethylaminoethyl)-7H-indole[2,3-c]-quinolin-6(5H)-one, lactose, corn starch and prehydrolyzed corn starch are blended in a suitable mixer.
2. The mixture is granulated to a heavy paste with water, and the moist mass is passed through a No. 12 screen. It is then dried overnight at 110° F.
3. The dried granules are passed through a No. 16 screen and transferred to a suitable mixer. The calcium stearate is added and mixed until uniform.
4. The mixture is then compressed at a tablet weight of 410 mg. using tablet punches having a diameter of approximately ⅝. (Tablets may be either flat or biconvex and may be scored if desired.)

EXAMPLE 89

Tablet Formulation

| Tablet Formulation | Per Tablet |
|---|---|
| 10-Chloro-5-(2-dimethylaminoethyl)-7H-indolo[2,3-c]quinolin-6(5H)-one | 500 mg. |
| Corn Starch | 30 mg. |
| Lactose | 88 mg. |
| Gelatin | 12 mg. |
| Talcum | 15 mg. |
| Magnesium Stearate | 5 mg. |
| Total Weight | 650 mg. |

Procedure:
1. The 10-chloro-5-(2-dimethylaminoethyl)-7H-indolo[2,3-c]-quinoline-6(5H)-one and lactose are thoroughly mixed in suitable blending equipment and granulated with a 10 percent gelatin solution.
2. The moist passed through a No. 12 screen, and the granules are dried on paper-line trays overnight.
3. The dried granules are passed through a No. 14 screen and placed in a suitable mixer. The talcum and magnesium stearate are added and blended.
4. Then, the granulation is compressed into tablets weighting approximately 650 mg. each, using punches having an approximate diameter of 12.7 mm. (½). The final tablet thickness if about 5.1 mm.

EXAMPLE 90

Preparation of
6,10-dichloro-7-(2-diethylaminoethyl)-7H-indolo-
[2,3-c]quinoline A mixture of 2.87 g. of 6,10-dichloro-7H-indolo[2,3-c]-quinoline, 720 mg. of sodium hydride (~50% dispersion in oil) and 25 ml. of dimethylformamide was stirred at room temperature for 0.5 hour.

To this mixture was added 5.0 ml. of a solution of diethylaminoethyl chloride (a 3.20M solution in toluene) and the mixture was stirred at room temperature for 1.5 hours.

The excess hydride was decomposed with water, and the resulting mixture was evaporated in vacuo. The residue was partitioned between ether and water. The ether layer was dried over anhydrous sodium sulfate, and evaporated to dryness in vacuo. The residue on crystallization from hexane, yielded 2.00 g. (52%) of 6,10-dichloro-7-(2-diethylaminoethyl)-7H-indolo-[2,3-c]quinoline as yellow prisms having a melting point of 83°–85°.

EXAMPLE 91

Preparation of
10-chloro-6-(2-diethylaminoethylamino)-7H-indolo-
[2,3-c]quinoline A mixture of 5.00 g. of 6,10-dichloro-7H-indolo[2,3-c]-quinoline and 5.0 ml. of N,N-diethylaminoethylamine was heated at 150° for 6 hours under nitrogen.

On cooling, the glassy brown viscous oil was dissolved in a minimum of ethanol by boiling. The ethanol insolubles were removed by filtration. The ethanolic solution was treated with ethanolic hydrogen bromide. The light yellow dihydrobromide formed was collected by filtration and washed with acetone. This salt was suspended in water, and was treated with 3N sodium hydroxide. The free base was extracted into ether. The ether layer was dried over anhydrous sodium sulfate, and evaporated to dryness in vacuo. The residue, on crystallization from acetonitrile, yielded 3.60 g. (57%) of 10-chloro-6-(2-diethylaminoethylamino)-7H-indolo[2,3-c]quinoline as yellow prisms having a melting point of 217°–219°.

EXAMPLE 92

Preparation of
10-chloro-5-(2-dimethylaminoethyl)-7-(2,3-oxido-
propyl)-7H-indolo[2,3-c]quinolin-6(5H)-one 10.2 G. of 10-chloro-5-(2-dimethylaminoethyl)-7H-indolo[2,3-c]-quinolin-6(5H)-one were dissolved in 900 ml. of dimethylformamide by heating to 90°. A 50 percent suspension of 6 g. of sodium hydride in mineral oil was washed with hexane and added to the mixture. After stirring for 5 minutes at 80°–90°, 6 g. of epibromohydrine was added and stirring was continued for 15 minutes. The reaction mixture was partitioned between toluene and aqueous sodium bicarbonate solution. The toluene layer was washed with water, dried over sodium sulfate, filtered and evaporated. The residue was partly dissolved in methylene chloride. The insoluble portion of starting material was separated by filtration, and the product was crystallized from the filtrate by addition of ether. The resulting product was further purified by chromatography over 200 g. of silica gel using 10 percent ethanol in methylene chloride for elution. Crystallization from methylene chloride/ether yielded 6 g. of 10-chloro-5-(2-dimethylaminoethyl)-7-(2,3-oxidopropyl)-7H-indolo[2,3-c]quinolin-6(5H)-one, having a melting point of 137°–139°.

EXAMPLE 93

Preparation of
10-chloro-7-(2,3-dihydroxypropyl)-5-(2-dimethyl-
aminoethyl)-7H-indolo[2,3-c]quinolin-6(5H)-one A mixture of 4 g. of 10-chloro-5-(2-dimethylaminoethyl)-7-(2,3-oxidopropyl)-7H-indolo[2,3-c]quinolin-6(5H)-one, 20 ml. of trifluoroacetic acid and 80 ml. of water was heated on the steam bath for 15 minutes. The hot solution was made alkaline by addition of ammonia and the product was extracted with methylene chloride. The extracts were washed with water, dried over sodium sulfate and evaporated. Crystallization of the residue from methylene chloride/ether yielded 4 g. of 10-chloro-7-(2,3-dihydroxypropyl)-5-(2-dimethylaminoethyl)-7H-indolo[2,3-c]quinolin-6(5H)-one, having a melting point of 172°–174°.

EXAMPLE 94

Preparation of
2-bromoethyl-5-chloro-3-(2-fluorophenyl)indole-2-
carboxylate

25 G. of phosphorus pentachloride were added to a suspension of 29 g. of 5-chloro-3-(2-fluorophenyl)indole-2-carboxylic acid in 500 ml. of methylene chloride. After stirring for 30 minutes at room temperature, the reaction mixture was washed with water, dried over sodium sulfate and evaporated. 50 Ml. of 2bromoethanol was added to the residue, and the mixture was heated on a steam bath for 30 minutes. The product was precipitated by the addition of water, collected and recrystallized from ether/ethanol to yield 24.5 g. of 2-bromoethyl-5-chloro-3-(2-fluorophenyl)-indole-2-carboxylate, having a melting point of 154°–155°.

EXAMPLE 95

Preparation of
8-chloro-10-(2-fluorophenyl)-3,4-dihydro-1H-[1,4]-
oxazino[4,3-a]indol-1-one 12.3 G. of potassium t-butoxide were added to a solution of 39.6 g. of 2-bromoethyl-5-chloro-3-(2-fluorophenyl)indole-2-carboxylate in 75 ml. of dry dimethylformamide. After stirring for 15 minutes at room temperature, the mixture was diluted with ice water. The precipitated product was collected and recrystallized from methylene chloride/ethanol to yield 14.2 g. of 8-chloro-10-(2-fluorophenyl)-3,4-dihydro-1H-[1,4]-oxazino[4,3-a]indol-1-one, having a melting point of 166°–169°. An analytical sample was recrystallized twice from the same solvents and had a melting point of 170°–172°.

EXAMPLE 96

Preparation of
10-chloro-5-(2-dimethylaminoethyl)-7-(2-hydroxy-
ethyl)-7H-indolo[2,3-c]quinolin-6(5H)-one A mixture of 14 g. of 8-chloro-10-(2-fluorophenyl)-3,4-dihydro-1H-[1,4]oxazino[4,3-a]indol-1-one and 50 ml. of 2-dimethylaminoethylamine was stirred and refluxed for 20 minutes. The excess amine was removed under reduced pressure and the residue, 15 g., was dissolved in 100 ml. of dimethylformamide. After addition of 6 g. of sodium hydride suspension (50 percent in mineral oil), the mixture was stirred and refluxed under an atmosphere of nitrogen for 15 minutes. The product was precipitated by addition of ice water to the reaction mixture. Thereafter, it was collected and recrystallized twice from methylene chloride/ethanol to yield 8.2 g. of 10-chloro-5-(2-dimethylaminoethyl)-7-(2-hydroxyethyl)-7H-indolo[2,3-c]quinolin-6(5H)-one, having a melting point of 201°–203°.

EXAMPLE 97

Preparation of 10-chloro-5-(2-dimethylaminoethyl)-7H-indolo-[2,3-c]quinolin-6(5H)-one hydrochloride A suspension of 3g. of 10-chloro-5-(2-dimethylaminoethyl)-7H-indolo[2,3-c]quinolin-6(5H)-one in 200 ml. of ethanol was heated to reflux. After the addition of 3 ml. of concentrated hydrochloric acid, refluxing was continued for 1 hour. The crystals which formed were collected, washed with ethanol and ether and dried to yield 3.1 g. of hydrochloride having a melting point of 327°–330°.

We claim:
1. A compound of the formula

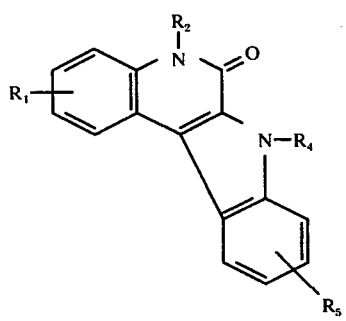

wherein $R_1$ and $R_5/$ , independently, are hydrogen, halogen, trifluoromethyl, lower alkyl of 1 of 7 carbon atoms, lower alkoxy of 1 to 7 carbon atoms, amino, cyano or nitro; $R_2$ and $R_4$, independently, are hydrogen, lower alkyl of 1 to 7 carbon atoms, cyano-lower alkyl wherein lower alkyl is of 1 to 7 carbon atoms, dihydroxy-lower alkyl of 1 to 7 carbon atoms, 2,3-epoxypropyl, lower alkenyl of 2 of 7 carbon atoms,

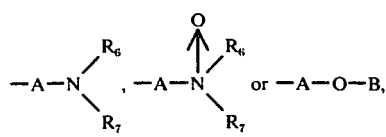

or -A—O-13 B, wherein A is a straight chain lower alkylene of 1–7 carbon atoms or a straight chain lower alkylene of 1 to 7 carbon atoms mono-substituted by lower alkyl of 1–7 carbon atoms, $R_6$ and $R_7$, independently, are hydrogen, lower alkyl of 1 to 7 carbon atoms, hydroxy-lower alkyl of 1 to 7 carbon atoms or halo-lower alkyl of 1 to 7 carbon atoms, or taken together with the nitrogen atom, are piperidino, piperazino, pyrrolidino, morpholino, imidazoline, 4-lower alkylpiperazino wherein lower alkyl is of 1–7 carbon atoms or methylpiperidino, and B is hydrogen, lower alkyl of 1 to 7 carbon atoms or lower alkanoyl of 1 to 7 carbon atoms; provided that at least one of $R_2$ or $R_4$ is

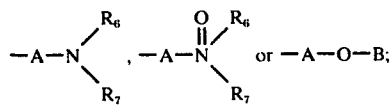

or an addition salt thereof with a pharmaceutically acceptable acid.

2. A compound of the formula

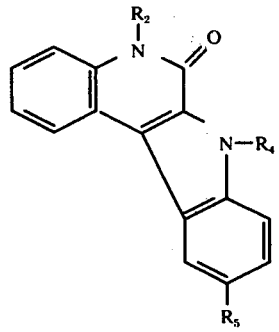

wherein $R_2$ and $R_4$, independently, are hydrogen, lower alkyl of 1 to 7 carbon atoms, hydroxy-lower alkyl of 1 to 7 carbon atoms, lower alkoxy of 1 to 7 carbon atoms, lower alkyl of 1 to 7 carbon atoms lower alkenyl of 2 to 7 carbon atoms or

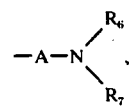

wherein A is a straight chain lower alkylene of 2–7 carbon atoms or straight chain lower alkylene of 2 to 7 carbon atoms mono- substituted by lower alkyl of 1 to 7 carbon atoms, and $R_6$ and $R_7$, independently, are hydrogen or lower alkyl of 1 to 7 carbon atoms, or taken together with the nitrogen atom, are piperidino, piperazino, pyrrolidino, morpholino, imidazoline, 4-lower alkylpiperazino wherein lower alkyl is of 1–7 carbon atoms or methylpiperidino; and $R_5$ is nitro, halogen, or trifluoromethyl; provided that one of $R_2$ or $R_4$ is

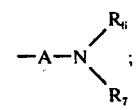

or an addition salt thereof with a pharmaceutically acceptable acid.

3. A compound is accordance with claim 2, wherein one of $R_2$ or $R_4$ is hydrogen and the other is

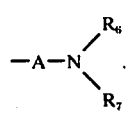

4. The compound in accordance with claim 3, 5-(2-dimethylaminoethyl)-7H-indolo[2,3-c]quinolin-6(5H)-one.

5. The compound in accordance with claim 3, 7-(2-diethylaminoethyl)-7H-indolo[2,3-c]quinolin-6(5H)-one.

6. A compound in accordance with claim 3, wherein R₅ is chloro.

7. The compound in accordance with claim 6, 10-chloro-5-(2-dimethylaminoethyl)-7H-indolo[2,3-c]quinolin-6(5H)-one.

8. The compound in accordance with claim 6, 10-chloro-5-(2-methylaminoethyl)-7H-indolo[2,3-c]quinolin-6(5H)-one.

9. The compound in accordance with claim 6, 10-chloro-5-(2-aminoethyl)-7H-indolo[2,3-c]quinolin-6(5H)-one.

10. The compound in accordance with claim 6, 10-chloro-7-(2-dimethylaminoethyl)-7H-indolo[2,3-c]quinolin-6(5H)-one.

11. A compound of the formula

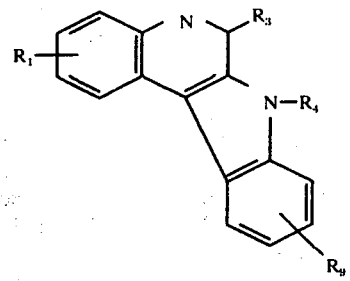

wherein R₁ is hydrogen, halogen, trifluoromethyl, lower alkyl of 1 to 7 carbon atoms, lower alkoxy of 1 to 7 carbon atoms, amino, cyano or nitro; R₃ is hydrogen, halogen, trifluoromethyl, hydrazino, lower alkyl of 1 to 7 carbon atoms, amino, lower alkylamino of 1 to 7 carbon atoms, di-lower alkylamino of 1 to 7 carbon atoms, lower alkoxy of 1 to 7 carbon atoms, lower alkoxyamino of 1 to 7 carbon atoms,

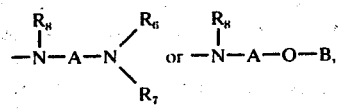

wherein A is a straight chain lower alkylene of 2–7 carbon atoms or a straight-chain lower alkylene of 2 to 7 carbon atoms mono-substituted by lower alkyl of 1 to 7 carbon atoms, R₆ and R₇, independently, are hydrogen, lower alkyl of 1 to 7 carbon atoms, hydroxy-lower alkyl of 1 to 7 carbon atoms or halo-lower alkyl of 1 to 7 carbon atoms, or taken together with the nitrogen atom, are piperidino, piperazino, pyrrolidino, morpholino, imidazoline, 4-lower alkylpiperazino wherein lower alkyl is of 1–7 carbon atoms or methylpiperidino, R₈ is hydrogen or lower alkyl of 1 to 7 carbon atoms and B is hydrogen, lower alkyl of 1 to 7 carbon atoms or lower alkanoyl of 1 to 7 carbon atoms; R₄ is hydrogen, lower alkyl of 1 to 7 carbon atoms,

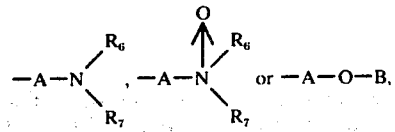

or -A-O-B, wherein A is a straight chain lower alkylene of 2-7 carbon atoms or a straight chain lower alkylene of 2-7 carbon atoms mono-substituted by lower alkyl of 1-7 carbon atoms, R₆ and R₇, independently, are hydrogen, lower alkyl of 1 to 7 carbon atoms, hydroxy-lower alkyl of 1 to 7 carbon atoms or halo-lower alkyl of 1 to 7 carbon atoms, or taken together with the nitrogen atom, are piperidino, piperazino, pyrrolidino, morpholino, imidazoline, 4-lower alkylpiperazino wherein lower alkyl is of 1–7 carbon atoms an methylpiperidino, and B is hydrogen, lower alkyl of 1 to 7 carbon atoms or lower alkanoyl of 1 to 7 carbon atoms; and R₉ is halogen, lower alkyl of 1 to 7 carbon atoms, lower alkoxy of 1 to 7 carbon atoms, amino, cyano or nitro; provided that at least one of R₃ or R₄ is a basic amino side chain or —A—O—B, or an addition salt thereof with a pharmaceutically acceptable acid.

12. In accordance with claim 11, a compound of the formula

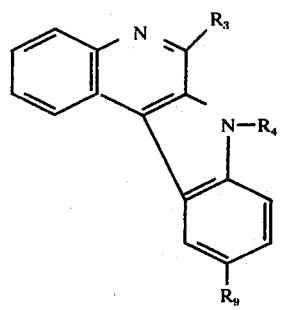

wherein R₃ is hydrogen, halogen, trifluoromethyl, hydrazino, lower alkyl of 1 to 7 carbon atoms, lower alkoxy of 1 to 7 carbon atoms, lower alkoxyamino of 1 to 7 carbon atoms or

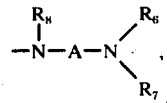

wherein A is a straight chain lower alkylene of 2–7 carbon atoms or a straight chain lower alkylene of 2 to 7 carbon atoms mono-substituted by lower alkyl of 1 to 7 carbon atoms, R₆ and R₇, independently, are hydrogen or lower alkyl of 1 to 7 carbon atoms, or taken together with the nitrogen atom, are piperidino, piperazino, pyrrolidino, morpholino, imidazoline, 4-lower alkylpiperazino wherein lower alkyl is of 1 to 7 carbon atoms or methylpiperidino, and R₈ is hydrogen or lower alkyl of 1 to 7 carbon atoms; R₄ is hydrogen or

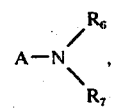

wherein A is a straight chain lower alkylene of 2–7 carbon atoms or a straight chain lower alkylene of 2 7 carbon atoms mono- substituted by lower alkyl of 1 to 7 carbon atoms, R₆ and R₇, independently, are hydrogen or lower alkyl of 1 to 7 carbon atoms, or taken together with the nitrogen atom, are piperidino, piperazino, pyrrolidino, morpholino, imidazoline, 4-lower alkylpiperazino wherein lower alkyl is of 1 to 7 carbon atoms or methylpiperidino and $R_9$ is nitro, halogen, or trifluoromethyl; provided that one of $R_3$ or $R_4$ is a basic amino side chain; or an addition salt thereof with a pharmaceutically acceptable acid.

13. A compound in accordance with claim 12, wherein one of $R_3$ or $R_4$ is hydrogen and the other is a basic amino side chain.

14. The compound in accordance with claim 13, 6,10-dichloro-7-(2-diethylaminoethyl)indolo[2,3-c]quinoline.

15. The compound in accordance with claim 13, 10-chloro-6-(2-diethylaminoethylamino)indolo[2,3-c]quinoline.

* * * * *